(12) United States Patent
Ju et al.

(10) Patent No.: US 8,476,432 B2
(45) Date of Patent: Jul. 2, 2013

(54) PROCESS FOR THE PREPARATION OF HMG-COA REDUCTASE INHIBITORS AND INTERMEDIATES THEREOF

(75) Inventors: Hyun Ju, Yongin-si (KR); Sang-Sun Joung, Hwaseong-si (KR); Hyun-Jik Yi, Yongin-si (KR); Ja-Heouk Khoo, Gunpo-si (KR); Jong-Chul Lim, Yongin-si (KR); Jae-Gyu Kim, Seoul (KR)

(73) Assignee: Yuhan Corporation, Seoul (KR)

( * ) Notice: Subject to any disclaimer, the term of this patent is extended or adjusted under 35 U.S.C. 154(b) by 0 days.

(21) Appl. No.: 13/806,626

(22) PCT Filed: Jun. 30, 2011

(86) PCT No.: PCT/KR2011/004783
§ 371 (c)(1),
(2), (4) Date: Dec. 21, 2012

(87) PCT Pub. No.: WO2012/002741
PCT Pub. Date: Jan. 5, 2012

(65) Prior Publication Data
US 2013/0096303 A1    Apr. 18, 2013

(30) Foreign Application Priority Data

Jul. 1, 2010   (KR) .................. 10-2010-0063604

(51) Int. Cl.
| C07D 239/42 | (2006.01) |
| C07D 215/12 | (2006.01) |
| C07D 405/06 | (2006.01) |
| C07D 209/10 | (2006.01) |
| C07D 257/04 | (2006.01) |

(52) U.S. Cl.
USPC ........... 544/297; 546/180; 546/135; 548/511; 548/468; 548/251

(58) Field of Classification Search
USPC ................... 544/297; 546/180, 135; 548/511, 548/468, 251
See application file for complete search history.

(56) References Cited

U.S. PATENT DOCUMENTS

| 5,011,930 A | 4/1991 | Fujikawa et al. |
| 5,102,888 A | 4/1992 | Fujikawa et al. |
| 5,185,328 A | 2/1993 | Fukikawa et al. |
| 5,260,440 A | 11/1993 | Hirai et al. |
| 5,354,772 A | 10/1994 | Kathawala |
| 5,854,259 A | 12/1998 | Fujikawa et al. |
| 5,856,336 A | 1/1999 | Fujikawa et al. |
| 5,872,130 A | 2/1999 | Fujikawa et al. |
| RE37,314 E | 8/2001 | Hirai et al. |
| 2006/0149065 A1 | 7/2006 | Kumar et al. |
| 2007/0255060 A1 | 11/2007 | Okada et al. |
| 2008/0161560 A1 | 7/2008 | Deshpande et al. |
| 2010/0029940 A1 | 2/2010 | Dandala et al. |
| 2010/0056783 A1 | 3/2010 | Satyanarayana Reddy et al. |
| 2011/0301348 A1 | 12/2011 | Okada et al. |

FOREIGN PATENT DOCUMENTS

| EP | 0 304 063 A2 | 2/1989 |
| EP | 0 521 471 A1 | 1/1993 |
| WO | 2005/042522 A1 | 5/2005 |
| WO | 2008/044243 A2 | 4/2008 |

*Primary Examiner* — Kristin Bianchi
(74) *Attorney, Agent, or Firm* — Vorys, Sater, Seymour and Pease LLP; Mih Suhn Koh

(57) ABSTRACT

The present invention provides an improved process for preparing HMG-CoA reductase inhibitors such as rosuvastatin calcium, fluvastatin sodium, and pitavastatin calcium under a mild condition, using a novel amide-bond-containing compound having $R_2$—N—O—$R_1$ moiety as a key intermediate. And also, the present invention provides the novel compound, an intermediate useful for the preparation thereof, and a process for the preparation thereof.

19 Claims, No Drawings

PROCESS FOR THE PREPARATION OF HMG-COA REDUCTASE INHIBITORS AND INTERMEDIATES THEREOF

TECHNICAL FIELD

The present invention relates to a process for preparing HMG-CoA reductase inhibitors using novel intermediates. And also, the present invention relates to the novel intermediate and a process for the preparation thereof.

BACKGROUND ART

HMG-CoA reductase inhibitors, such as rosuvastatin calcium, fluvastatin sodium, pitavastatin calcium, are known as a drug useful for reducing LDL-cholesterol and triglyceride level (for example, EP0521471, U.S. Pat. No. 5,354,772, EP 0304063, and etc). The chemical name of rosuvastatin calcium is E-7-[2-(N-methyl-N-methanesulfonylamino)-4-(4-fluorophenyl)-6-isopropyl-pyrimidin-5-yl]-(3R,5S)-3,5-dihydroxyhept-6-enoic acid 1/2 calcium salt. The chemical name of fluvastatin sodium is (3R,5S,6E)-7-[3-(4-fluorophenyl)-1-isopropyl-1H-indol-2-yl]-3,5-dihydroxy hept-6-enoic acid sodium salt. The chemical name of pitavastatin calcium is (3R,5S,6E)-7-[2-cyclopropyl-4-(4-fluorophenyl)quinolin-3-yl]-3,5-dihydroxy hept-6-enoic acid 1/2 calcium salt. They have the following chemical structures of Formula 1a (rosuvastatin calcium), Formula 1b (fluvastatin sodium), and Formula 1c (pitavastatin calcium), respectively.

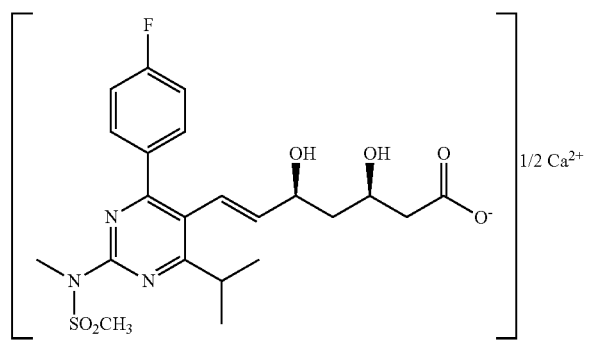

<Formula 1a>

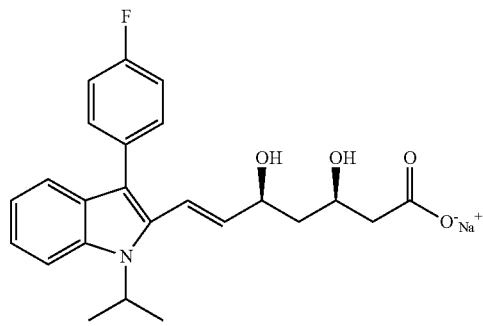

<Formula 1b>

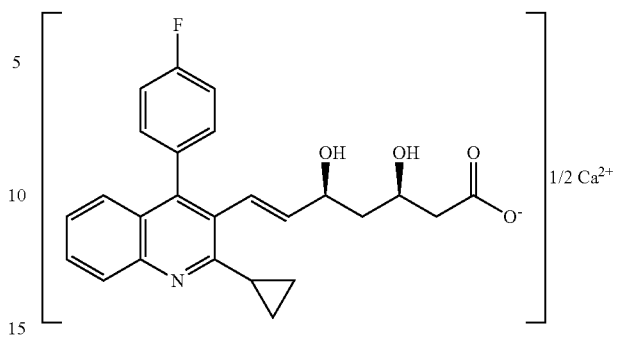

<Formula 1c>

For example, a process for preparing rosuvastatin or its salt has been disclosed in EP0521471. The process described in EP0521471 involves preparing an ester-bond-containing compound through Wittig Reaction and preparing a dihydroxy-group-containing intermediate under reduction condition using very low temperature. And also, the process involves preparing rosuvastatin sodium salt through hydrolysis of the dihydroxy-group-containing intermediate, converting the sodium salt to its calcium salt. In the process, both the ester-bond-containing compound and the dihydroxy-group-containing intermediate have liquidic forms and require purifying with silica gel column chromatography, in order to remove impurities derived from the reactions, which makes the process not suitable for industrial mass production. Because the reduction for preparing the dihydroxy-group-containing intermediate should be performed under very low temperature condition and also requires using diethylmethoxyborane and sodium borohydride which are very explosive and toxic, it is difficult to apply the process to industrial mass production.

As an improved process for preparing rosuvastatin calcium, WO 2000/049014 has disclosed a process involving preparing a t-butyl ester bond-containing compound via Horner-Emmons Reaction; deprotecting the protecting group under acidic condition to obtain a diol-containing intermediate; hydrolyzing the intermediate under basic condition to obtain rosuvastatin sodium salt; purifying the sodium salt by converting to rosuvastatin methylamine salt followed by filtering; and converting to rosuvastatin calcium. And also, WO 2008/044243 has disclosed a process for preparing rosuvastatin calcium, using an amide-bond-containing compound having alkyl-substituted amine moiety, instead of the t-butyl ester bond-containing compound.

Meanwhile, WO 2005/042522 has disclosed a process for preparing rosuvastatin calcium via a lactone ring-containing intermediate from an ester bond-containing compound. However, in order to prepare the lactone ring-containing intermediate from an ester bond-containing compound according to WO 2005/042522, the process requires (1) hydrolyzing under acidic condition to deprotect the hydroxyl-protecting group, (2) rehydrolyzing under alkaline condition (e.g., sodium hydroxide used) to hydrolyze the ester-bond, and (3) cyclizing under acidic condition using severe condition (i.e., at 105° C.). Therefore, for preparing the lactone ring-containing intermediate, it is necessary to perform multiple steps, including cyclization under severe condition, which makes the process not suitable for industrial mass production.

DETAILED DESCRIPTION OF THE INVENTION

Technical Problem

The present invention provides an improved process for preparing HMG-CoA reductase inhibitors such as rosuvastatin calcium, fluvastatin sodium, and pitavastatin calcium, under a mild condition, using a novel amide-bond-containing compound having $R_2$—N—O—$R_1$ moiety as a key intermediate.

Therefore, it is an object of the present invention to provide an improved process for preparing HMG-CoA reductase inhibitors using the novel key intermediate.

It is another object of the present invention to provide the novel key intermediate and a process for the preparation thereof.

It is still another object of the present invention to provide a novel intermediate useful for preparing the key intermediate.

It is still another object of the present invention to provide a novel intermediate derived from the novel key intermediate, which is useful for preparing HMG-CoA reductase inhibitors.

Technical Solution

According to an aspect of the present invention, there is provided a process for preparing a compound of Formula 1, which comprises converting a compound of Formula 4 to a compound of Formula 1:

<Formula 1>

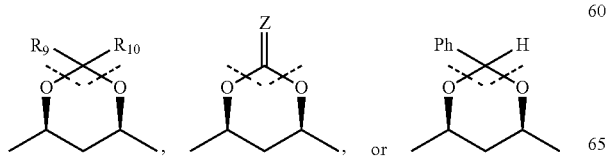

<Formula 4>

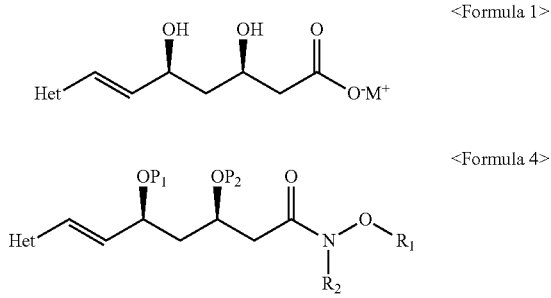

wherein,

M is an alkali metal or an alkaline earth metal, $R_1$ and $R_2$ are independently $C_1$~$C_5$ alkyl or aryl, $P_1$ and $P_2$ are independently an alcohol-protecting group; or $P_1$ and $P_2$ are cyclized each other to form any one of the following 1,3-diol protecting group, wherein $R_9$ and $R_{10}$ are independently $C_1$~$C_{10}$ alkyl or $R_9$ and $R_{10}$ are cyclized each other to form a pentane ring, a hexane ring, or a heptane ring; Z is oxygen or sulfur; and Ph is phenyl),

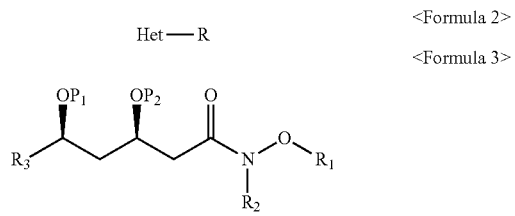

Het is

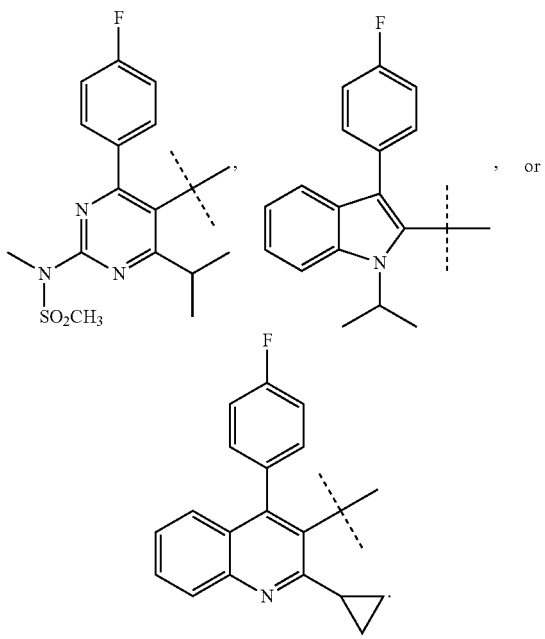

According to another aspect of the present invention, there is provided a compound of Formula 4:

<Formula 4>

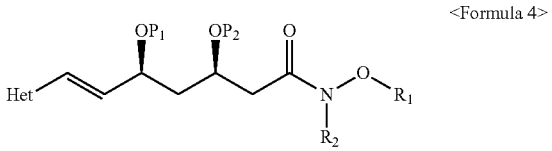

wherein, $R_1$, $R_2$, $P_1$, $P_2$ and Het are the same as defined in the above.

According to still another aspect of the present invention, there is provided a process for preparing a compound of Formula 4, which comprises reacting a compound of Formula 2 and a compound of Formula 3:

<Formula 2>

Het—R

<Formula 3> wherein, $R_1$, $R_2$, $P_1$, $P_2$ and Het are the same as defined in the above, R is —CHO, —$CH_2P(R_4)_3Br$, —$CH_2PO(R_4)_2$ or —$CH_2SO_2R_5$, wherein $R_4$ is $C_1$~$C_6$ alkyl, $C_1$~$C_6$ alkoxy, or aryl, $R_5$ is one of the following groups (wherein $R_6$ is $C_1$~$C_6$ alkyl, aryl, aryl-$C_1$~$C_6$ alkyl, or $C_3$~$C_6$ cycloalkyl; $R_7$ is hydrogen, $C_1$~$C_6$ alkyl, aryl, aryl-$C_1$~$C_6$ alkyl, halogen, trifluoromethyl, or nitro; $R_8$ is hydrogen, $C_1$~$C_6$ alkyl, $C_1$~$C_6$ alkoxy, $C_1$~$C_6$ alkyl substituted with halogen, or $C_1$~$C_6$ alkoxy mono- or disubstituted with halogen; X is oxygen, nitrogen, or sulfur)

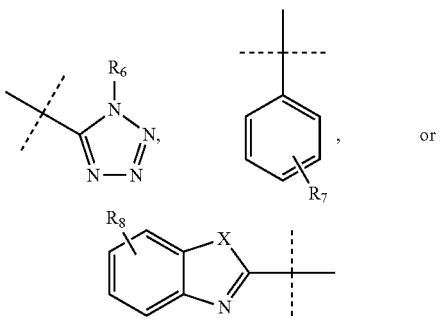

$R_3$ is —CHO or —CH$_2$SO$_2$R$_5$ (wherein, R$_5$ is the same as defined in the above).

According to still another aspect of the present invention, there is provided a compound of Formula 3 useful for preparing the compound of Formula 4:

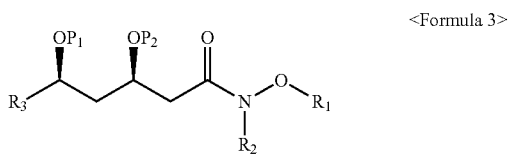

<Formula 3> wherein, $R_1$, $R_2$, $P_1$ and $P_2$ are the same as defined in the above, and $R_3$ is —CH$_2$SO$_2$R$_5$ (wherein, R$_5$ is the same as defined in the above).

According to still another aspect of the present invention, there is provided a compound of Formula 6 derived from the compound of Formula 4, which is useful for preparing HMG-CoA reductase inhibitors:

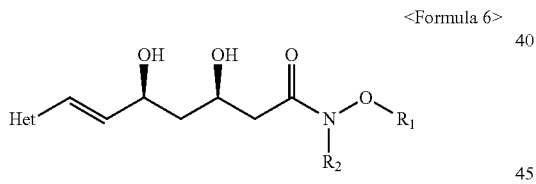

<Formula 6> wherein, $R_1$, $R_2$, and Het are the same as defined in the above.

Advantageous Effects

It is newly found, by the present invention, that HMG-CoA reductase inhibitors such as rosuvastatin calcium, fluvastatin sodium, and pitavastatin calcium may be prepared under a mild condition, by using a novel amide-bond-containing compound having R$_2$—N—O—R$_1$ moiety as a key intermediate.

In an embodiment, it is possible to perform both deprotection of a diol-protecting group (e.g., acetonide) and hydrolysis of the amide bond, by reacting the compound of Formula 4 with an acid. That is, since the compound of Formula 5 may be prepared through 1-step reaction for both deprotection and hydrolysis, the process of the present invention can avoid any impurity formation, which may be derived from deprotection in an acidic condition and hydrolysis in a basic condition; and also reduce the reaction steps therefor. Further, the reaction step for preparing the compound of Formula 5 through 1-step reaction can be performed under mild condition, i.e., at 50~60° C., and the product thereof can be easily isolated, e.g., using extraction, which make the process of the present invention suitable for industrial mass production.

And also, it is newly found that the compound of Formula 4 of trans-form can be selectively prepared by reacting the compound of Formula 2 and the compound of Formula 3. Therefore, when deprotection and hydrolysis of the compound of Formula 4 are sequentially performed, it is possible to accomplish very high steroselectivities of the resulting intermediates (e.g., compound of Formula 6) and the products (i.e., HMG-CoA reductase inhibitors such as rosuvastatin calcium, fluvastatin sodium, and pitavastatin calcium).

BEST MODE FOR CARRYING OUT THE INVENTION

The present invention provides a process for preparing a compound of Formula 1, which comprises converting a compound of Formula 4 to a compound of Formula 1:

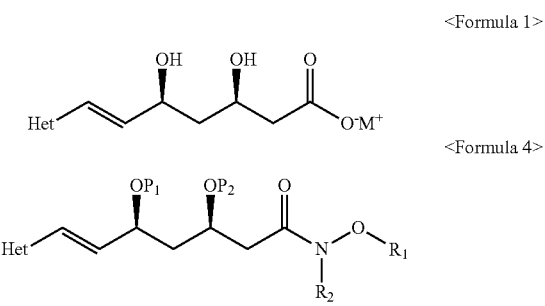

<Formula 1>

<Formula 4> wherein,

M is an alkali metal or an alkaline earth metal, $R_1$ and $R_2$ are independently $C_1$~$C_5$ alkyl or aryl, $P_1$ and $P_2$ are independently an alcohol-protecting group; or $P_1$ and $P_2$ are cyclized each other to form any one of the following 1,3-diol protecting group, wherein $R_9$ and $R_{10}$ are independently $C_1$~$C_{10}$ alkyl or $R_9$ and $R_{10}$ are cyclized each other to form a pentane ring, a hexane ring, or a heptane ring; Z is oxygen or sulfur; and Ph is phenyl),

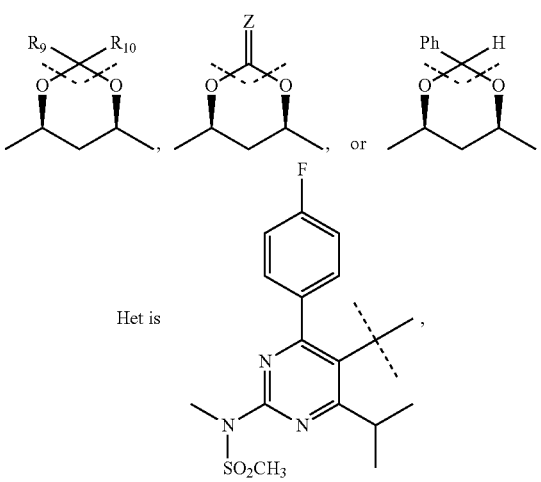

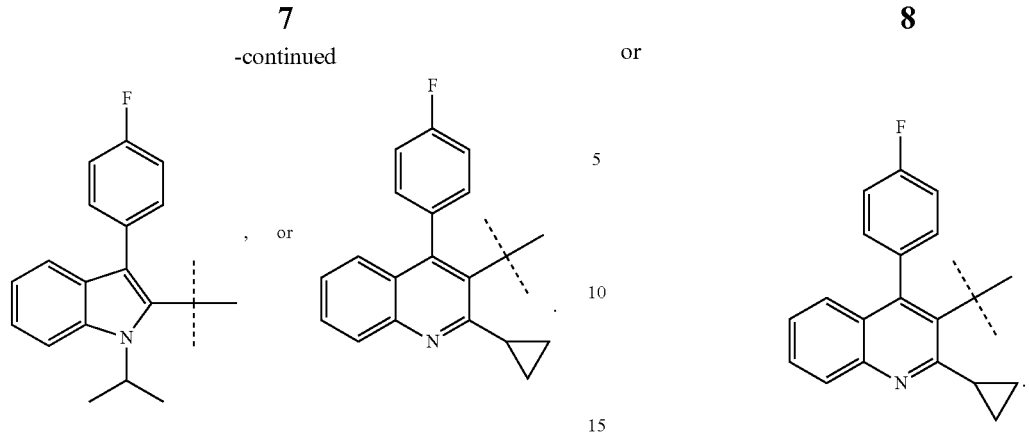

In an embodiment, the process of the present invention may comprise obtaining the compound of Formula 5 from the compound of Formula 4, followed by converting the compound of Formula 5 to the compound of Formula 1, as shown in the following Reaction Scheme 1.

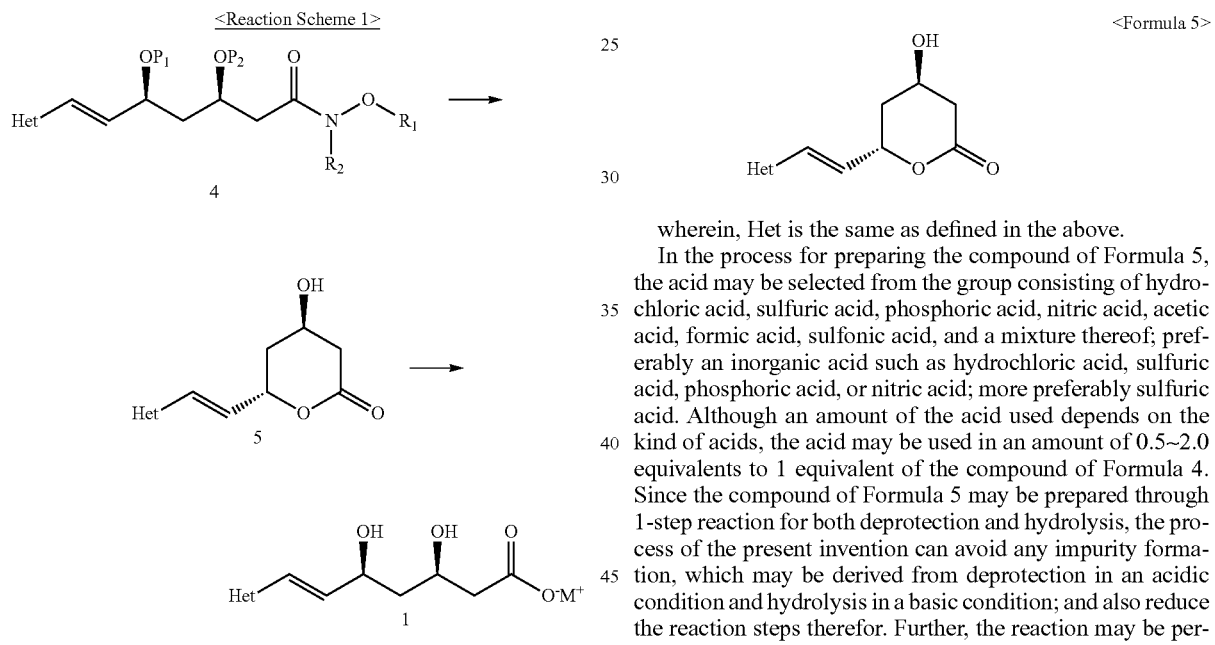

In the above Reaction Scheme 1, M, $R_1$, $R_2$, $P_1$, $P_2$, and Het are the same as defined in the above. Preferably, Het is

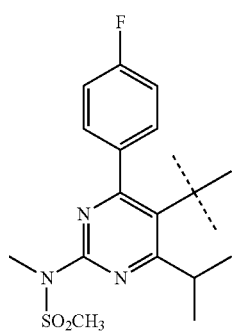

or

The process of the present invention may comprise reacting the compound of Formula 4 with an acid to obtain a compound of Formula 5; and reacting the compound of Formula 5 with an alkali metal hydroxide or an alkaline earth metal hydroxide to obtain the compound of Formula 1:

<Formula 5> wherein, Het is the same as defined in the above.

In the process for preparing the compound of Formula 5, the acid may be selected from the group consisting of hydrochloric acid, sulfuric acid, phosphoric acid, nitric acid, acetic acid, formic acid, sulfonic acid, and a mixture thereof; preferably an inorganic acid such as hydrochloric acid, sulfuric acid, phosphoric acid, or nitric acid; more preferably sulfuric acid. Although an amount of the acid used depends on the kind of acids, the acid may be used in an amount of 0.5~2.0 equivalents to 1 equivalent of the compound of Formula 4. Since the compound of Formula 5 may be prepared through 1-step reaction for both deprotection and hydrolysis, the process of the present invention can avoid any impurity formation, which may be derived from deprotection in an acidic condition and hydrolysis in a basic condition; and also reduce the reaction steps therefor. Further, the reaction may be performed at 0~80° C., preferably 40~70° C., more preferably 50~60° C. Therefore, since the process of the present invention may be carried out under mild condition, it is very suitable for industrial mass production. The reaction may be performed in the presence of a solvent selected from the group consisting of water, $C_1$~$C_{10}$ alcohol (for example, methanol, ethanol, isopropanol, butanol, etc.), tetrahydrofuran, acetonitrile, and a mixture thereof; preferably in the presence of acetonitrile.

The compound of Formula 5 produced from the reaction of the compound of Formula 4 and an acid may be easily isolated according to an extraction method using an organic solvent, e.g., ethyl acetate. If necessary, an isolation process using anti-solvent may be further carried out. For example, the isolation process may be performed by precipitating the product using $C_1$~$C_5$ alcohol (e.g., methanol, ethanol, isopropanol, butanol). In an embodiment, isopropanol may be used. Although an amount of the anti-solvent used is not specifically limited, the anti-solvent may be used for example 2~20 times, preferably 3~8 times by weight, to the compound of Formula 5. The isolation process may be performed at 0~60° C., preferably at 20~30° C., more preferable at room temperature (about 25° C.).

The reaction of compound of Formula 5 with an alkali metal hydroxide or an alkaline earth metal hydroxide may be performed preferably in an aqueous medium, e.g., in water. Therefore, the process of the present invention may minimize any environmental contamination derived from the use of an organic solvent. The alkali metal hydroxide or the alkaline earth metal hydroxide may be used in an amount of 1.0~1.5 equivalents to 1 equivalent of the compound of Formula 5. And, the reaction may be performed at 20~60° C., preferably at 20~30° C., more preferable at room temperature (about 25° C.). The resulting compound of Formula 1 may be isolated according to a conventional method, for example filtration under reduced pressure.

In another embodiment of the present invention, the process of the present invention may comprises performing the reactions for deprotection and hydrolysis sequentially, as shown in the following Reaction Scheme 2:

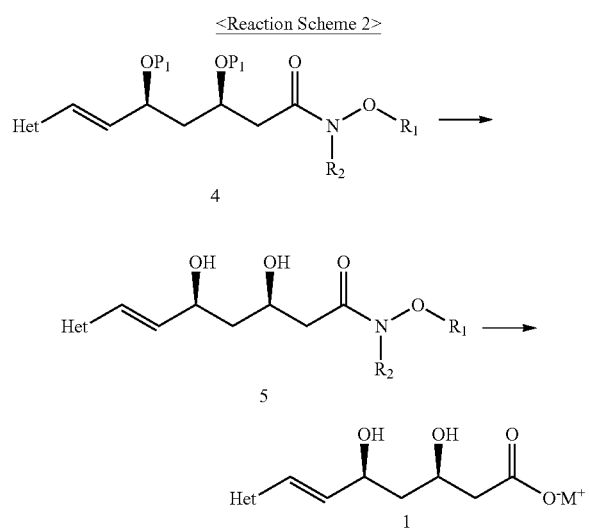

In the above Reaction Scheme 2, M, $R_1$, $R_2$, $P_1$, $P_2$, and Het are the same as defined in the above.

That is, the process of the present invention may comprise reacting the compound of Formula 4 with an acid to obtain a compound of Formula 6; and hydrolyzing the compound of Formula 6:

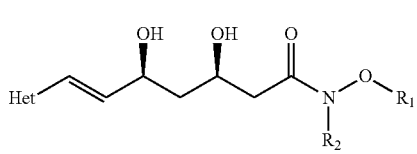

<Formula 6> wherein, $R_1$, $R_2$, and Het are the same as defined in the above.

The compound of Formula 6 is a novel compound. Therefore, the present invention comprises, within its scope, the compound of Formula 6. In an embodiment, the compound of Formula 6 may be the following compound of Formula 6a:

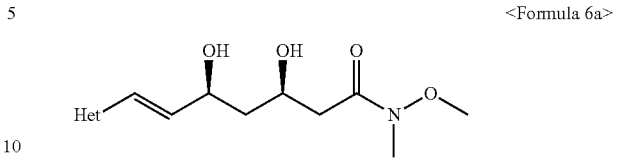

<Formula 6a> wherein, Het is the same as defined in the above.

In the process for preparing the compound of Formula 6 (i.e., deprotection process), the acid may be selected from the group consisting of hydrochloric acid, sulfuric acid, phosphoric acid, nitric acid, acetic acid, formic acid, sulfonic acid, and a mixture thereof; preferably an inorganic acid such as hydrochloric acid, sulfuric acid, phosphoric acid, or nitric acid; more preferably hydrochloric acid. The acid may be used in a catalytic amount. Typically, the acid may be used in an amount of 0.005~0.2 equivalents to 1 equivalent of the compound of Formula 4, but not limited to. And also, the reaction may be performed at 20~80° C., preferably 30~50° C., more preferably about 40° C. Therefore, since the process of the present invention may be carried out under mild condition, it is very suitable for industrial mass production. The reaction may be performed in the presence of a solvent selected from the group consisting of water, $C_1$~$C_{10}$ alcohol (for example, methanol, ethanol, isopropanol, butanol, etc.), acetonitrile, tetrahydrofuran, and a mixture thereof; preferably in the presence of acetonitrile. The compound of Formula 6 produced from the reaction of the compound of Formula 4 and an acid may be easily isolated through extraction and drying. The extraction may be performed using an organic solvent such as dichloromethane or ethyl acetate. The drying may be performed according to a conventional method, e.g., drying under reduced pressure. If necessary, before performing the extraction, the reaction mixture may be concentrated according to a conventional method, e.g., concentration under reduced pressure.

The hydrolysis of the compound of Formula 6 may be performed by reacting the compound of Formula 6 with an alkali metal hydroxide or an alkaline earth metal hydroxide. In an embodiment, the hydrolysis may comprise obtaining the product in an alkali metal salt form by reacting the compound of Formula 6 with an alkali metal hydroxide. In another embodiment, the hydrolysis may comprise obtaining the product in an alkaline earth metal salt form by reacting the compound of Formula 6 with an alkaline earth metal hydroxide.

If necessary, after the hydrolysis of the compound of Formula 6, the process of the present invention may further comprise forming an amine salt; and then forming an alkali metal salt or an alkaline earth metal salt. For example, after performing hydrolysis of the compound of Formula 6 produced from the compound of Formula 4, the process of the present invention may further comprise (i) reacting the hydrolyzed product of the compound of Formula 6 with an amine (for example, diisopropylamine, etc.) to obtain an amine salt; and (ii) reacting the amine salt with an alkali metal hydroxide or an alkaline earth metal hydroxide to form an alkali metal salt or an alkaline earth metal salt, as shown in the following Reaction Scheme 3.

<Reaction Scheme 3>

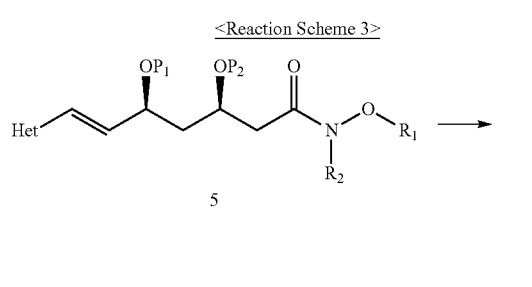

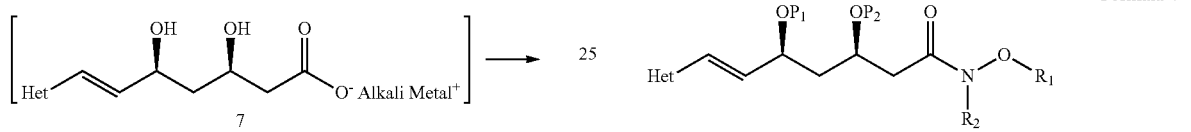

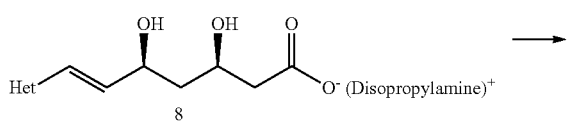

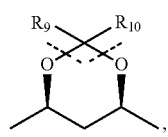

In the above Reaction Scheme 3, M, $R_1$, $R_2$, $P_1$, $P_2$, and Het are the same as defined in the above.

In the compound of Formula 4 used in the process of the present invention as a key intermediate, $R_1$ and $R_2$ may be independently methyl, ethyl, n-propyl, isopropyl, or phenyl; and $P_1$ and $P_2$ may be cyclized each other to form wherein $R_9$ and $R_{10}$ are independently $C_1$~$C_{10}$ alkyl. In an embodiment, the compound of Formula 4 may be the following compound of Formula 4a.

<Formula 4a>

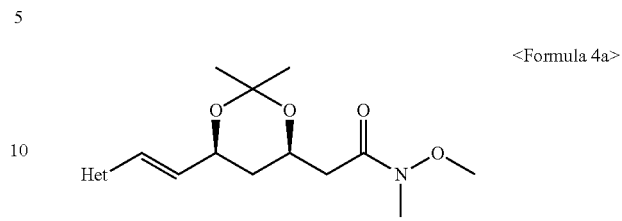

wherein, Het is the same as defined in the above.

The present invention also provides the compound of Formula 4 useful as an intermediate for preparing HMG-CoA reductase inhibitors such as rosuvastatin calcium, fluvastatin sodium, and pitavastatin calcium.

<Formula 4>

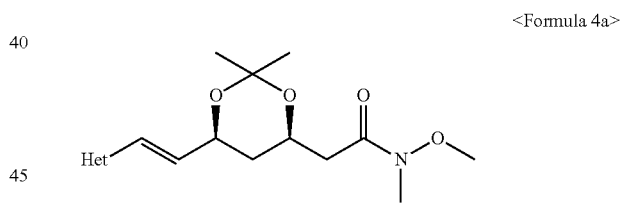

wherein, $R_1$, $R_2$, $P_1$, $P_2$ and Het are the same as defined in the above.

Since the compound of Formula 4 is very stable, no special caution is required for reaction and/or storage. In the compound of Formula 4, the following compound of Formula 4a is more preferable.

<Formula 4a>

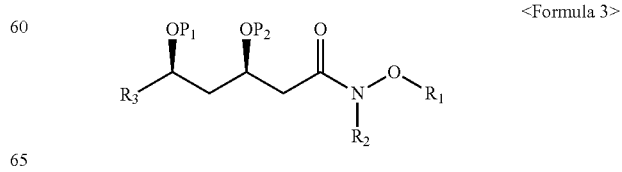

wherein, Het is the same as defined in the above.

The present invention also provides a process for preparing the compound of Formula 4. That is, the present invention provides a process for preparing a compound of Formula 4, which comprises reacting a compound of Formula 2 and a compound of Formula 3:

<Formula 2>

Het—R

<Formula 3> wherein, $R_1$, $R_2$, $P_1$, $P_2$ and Het are the same as defined in the above, R is —CHO, —CH$_2$P(R$_4$)$_3$Br, —CH$_2$PO(R$_4$)$_2$ or —CH$_2$SO$_2$R$_5$, wherein R$_4$ is C$_1$~C$_6$ alkyl, C$_1$~C$_6$ alkoxy, or aryl, R$_5$ is one of the following groups (wherein R$_6$ is C$_1$~C$_6$ alkyl, aryl, aryl-C$_1$~C$_6$ alkyl, or C$_3$~C$_6$ cycloalkyl; R$_7$ is hydrogen, C$_1$~C$_6$ alkyl, aryl, aryl-C$_1$~C$_6$ alkyl, halogen, trifluoromethyl, or nitro; R$_8$ is hydrogen, C$_1$~C$_6$ alkyl, C$_1$~C$_6$ alkoxy, C$_1$~C$_6$ alkyl compound of Formula 3 to obtain a compound of Formula 4; reacting the compound of Formula 4 with an acid to obtain a compound of Formula 6; and hydrolyzing the compound of Formula 6.

The compound of Formula 2 and compound of Formula 3 may be prepared according to or modifying the processes disclosed in WO2005/042522 and/or WO2008/044243. For example, the compound of Formula 3 may be prepared according to the following Reaction Scheme 4, 5, 6, or 7.

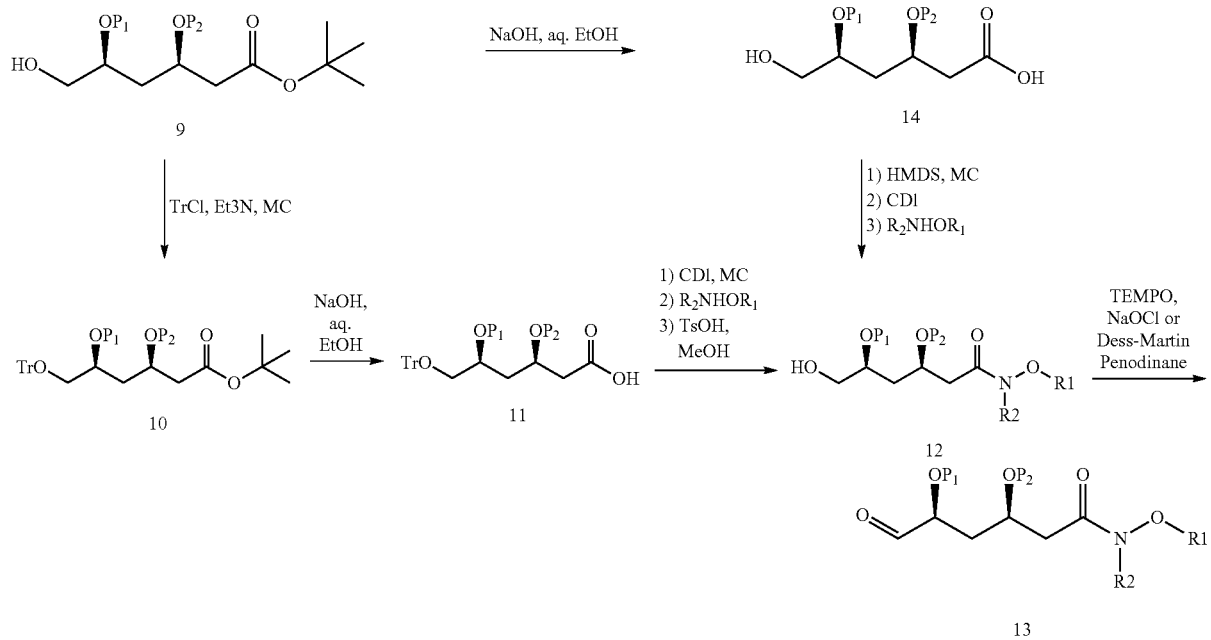

substituted with halogen, or C$_1$~C$_6$ alkoxy mono- or disubstituted with halogen; X is oxygen, nitrogen, or sulfur)

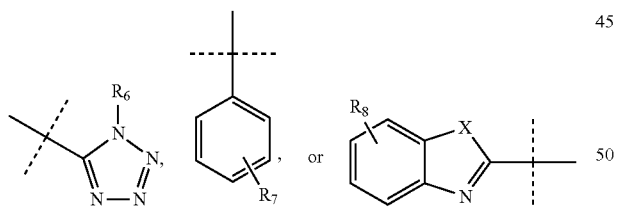

R$_3$ is —CHO or —CH$_2$SO$_2$R$_5$ (wherein, R$_5$ is the same as defined in the above).

It is newly found that the compound of Formula 4 of trans-form can be selectively prepared by reacting the compound of Formula 2 and the compound of Formula 3. Therefore, when deprotection and hydrolysis of the compound of Formula 4 are sequentially performed, it is possible to accomplish very high steroselectivities of the resulting intermediates (e.g., compound of Formula 6) and the products (i.e., HMG-CoA reductase inhibitors such as rosuvastatin calcium, fluvastatin sodium, and pitavastatin calcium). Therefore, in still another embodiment of the present invention, there is provided a process for preparing a compound of Formula 1, which comprises reacting a compound of Formula 2 and a

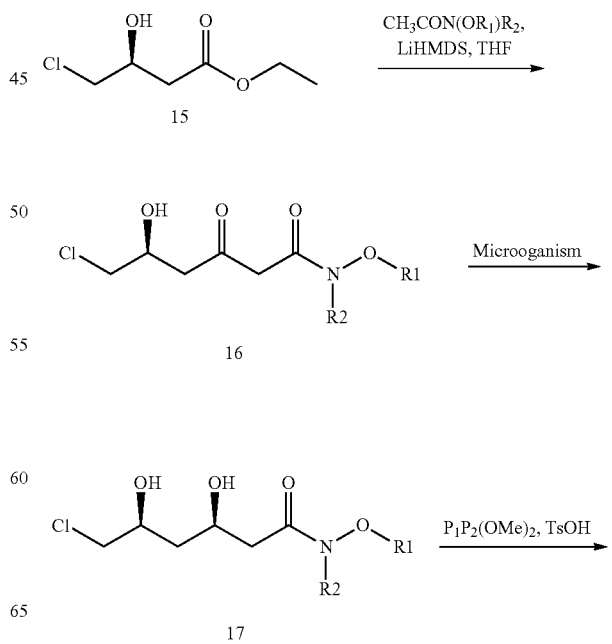

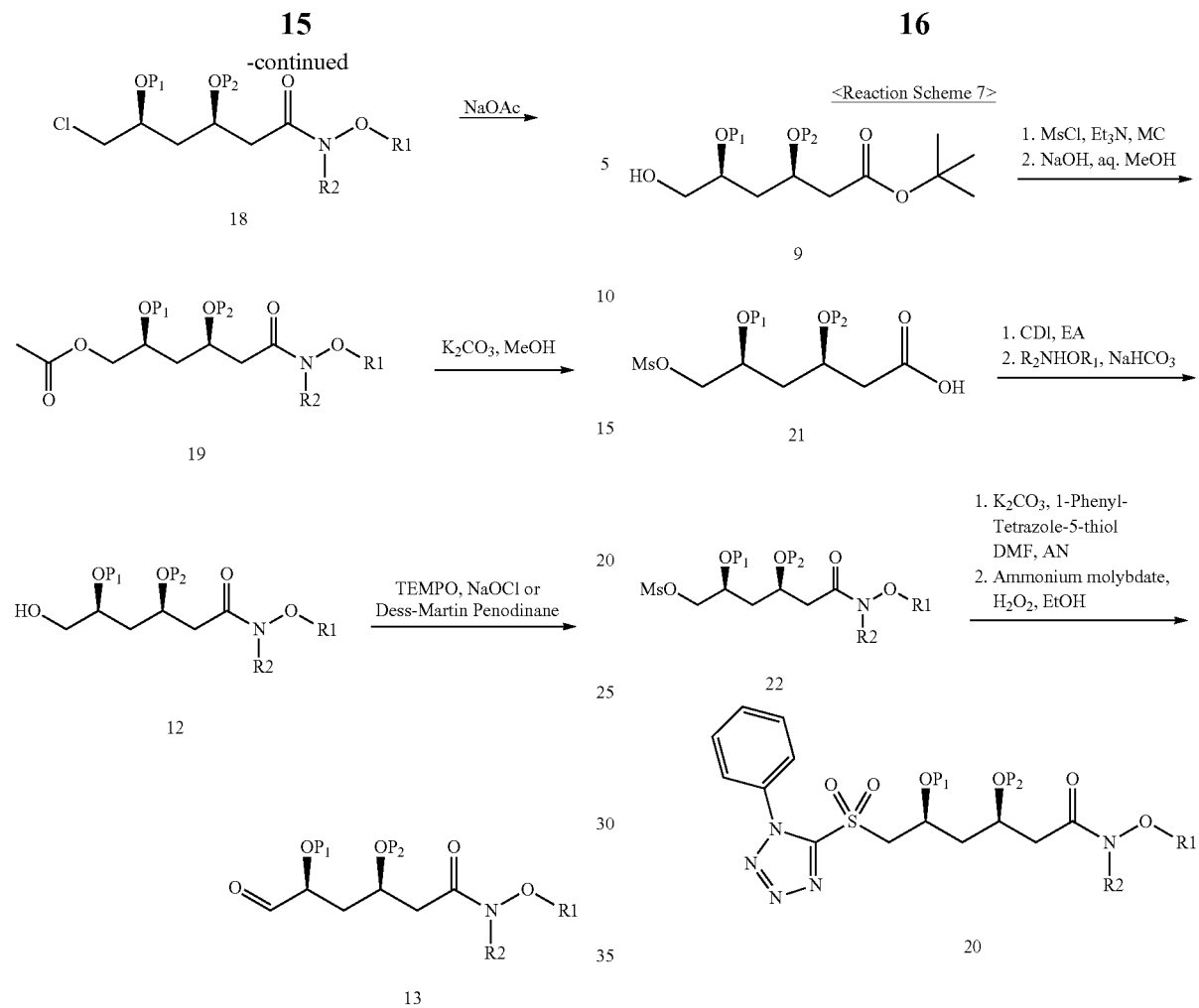
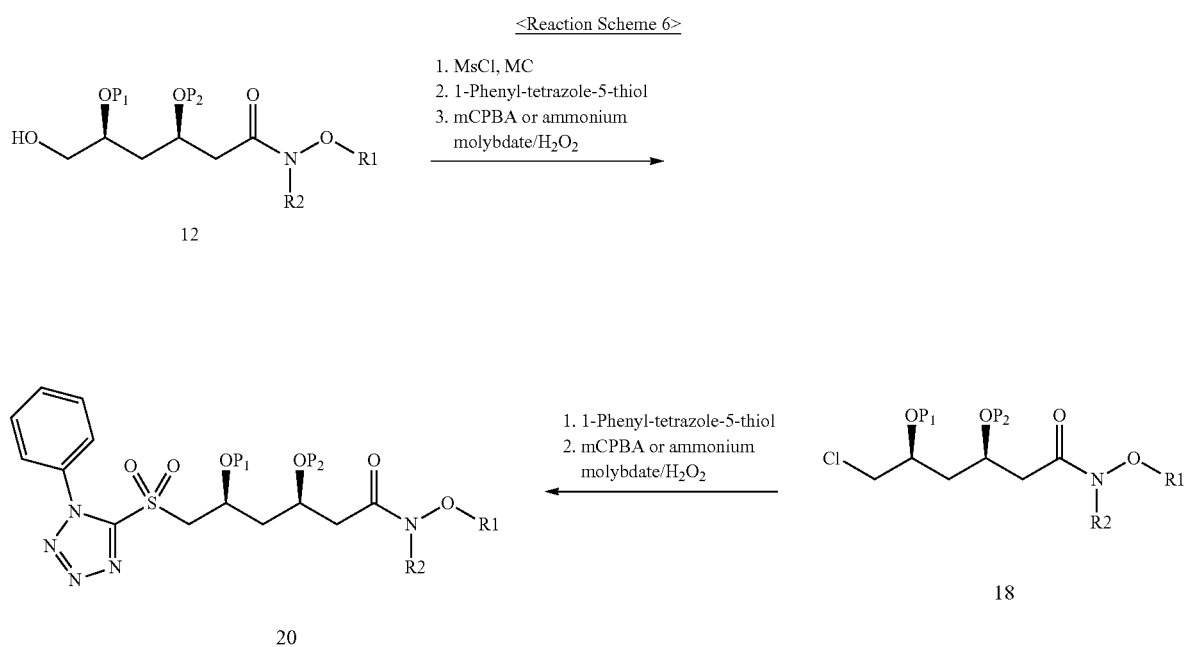
And also, for example, the compound of Formula 2 may be prepared according to the following Reaction Scheme 8.

<Reaction Scheme 8>

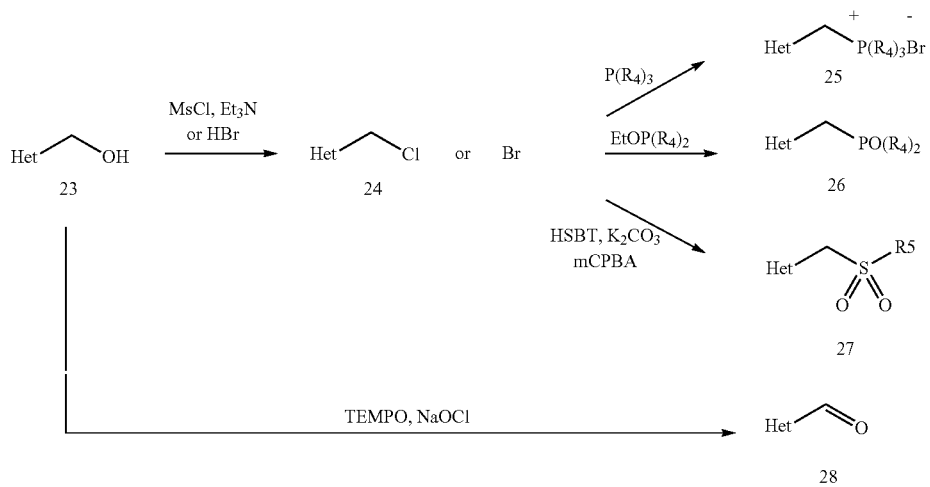

The reaction of compound of Formula 2 and the compound of Formula 3 may be performed via Wittig Reaction, Horner-Emmons Reaction, or Julia-Kocienski reaction.

For example, when R is —CH$_2$P(R$_4$)$_3$Br and R$_3$ is —CHO, the reaction of compound of Formula 2 and the compound of Formula 3 may be performed via Wittig Reaction. When R is —CH$_2$PO(R$_4$)$_2$ and R$_3$ is —CHO, the reaction of compound of Formula 2 and the compound of Formula 3 may be performed via Horner-Emmons Reaction. When R is —CH$_2$SO$_2$R$_5$ and R$_3$ is —CHO, the reaction of compound of Formula 2 and the compound of Formula 3 may be performed via Julia-Kocienski reaction. And also, when R is —CHO and R$_3$ is —CH$_2$SO$_2$R$_5$, the reaction of compound of Formula 2 and the compound of Formula 3 may be performed via Julia-Kocienski reaction.

The reaction of the compound of Formula 2 and the compound of Formula 3 via Wittig Reaction, Horner-Emmons Reaction, or Julia-Kocienski reaction may be preferably performed in the presence of a base. The base may be an inorganic base such as sodium C$_1$~C$_6$ alkoxide, potassium C$_1$~C$_6$ alkoxide, sodium carbonate, potassium carbonate, lithium carbonate, cesium carbonate, sodium bicarbonate, potassium bicarbonate, potassium phosphate; or an organic base such as 1,8-diazabicyclo[5.4.0]undec-7-ene (DBU), 1,4-diazabicyclo[2.2.2]octane (DABCO), 1,5-diazabicyclo[4.3.0]non-5-ene (DBN), pyridine, dimethylaminopyridine, triethylamine. And also, the base may be selected from the group consisting of lithium bis(trimethylsilyl)amide, sodium bis(trimethylsilyl)amide, potassium bis(trimethylsilyl)amide, butyllithium, sodium hydride, and a mixture thereof. The reaction of the compound of Formula 2 and the compound of Formula 3 may be carried out in an inert polar solvent. For example, the inert polar solvent may selected from group consisting of dimethylformamide, dimethylacetamide, dichloromethane, dimethyl sulfoxide, tetrahydrofuran, hexamethylphosphoramide, C$_1$~C$_4$ alcohol, dimethyl ether, diethyl ether, diisopropyl ether, ethyl acetate, dimethoxyethane, toluene, and a mixture thereof.

In an embodiment, when R is —CH$_2$P(R$_4$)$_3$Br and R$_3$ is —CHO, the reaction of the compound of Formula 2 and the compound of Formula 3 may be carried out using sodium carbonate or potassium carbonate as a base; and dimethylformamide or dimethylacetamide as a solvent. The reaction may be performed at a temperature ranging 20~120° C.

In another embodiment, when R is —CH$_2$PO(R$_4$)$_2$ and R$_3$ is —CHO, the reaction of the compound of Formula 2 and the compound of Formula 3 may be carried out using lithium bis(trimethylsilyl)amide, sodium bis(trimethylsilyl)amide, or potassium bis(trimethylsilyl)amide as a base; and tetrahydrofuran, dimethoxyethane, toluene, or a mixture thereof as a solvent. The reaction may be performed at a temperature ranging –90~20° C., preferably –70~10° C.

In still another embodiment, when R is —CH$_2$SO$_2$R$_5$ and R$_3$ is —CHO, the reaction of the compound of Formula 2 and the compound of Formula 3 may be carried out using sodium carbonate, potassium carbonate, or sodium bis(trimethylsilyl)amide as a base; and dimethylformamide, dimethylacetamide or tetrahydrofuran as a solvent. The reaction may be performed at a temperature ranging –90~20° C., preferably –70~10° C.

In still another embodiment, when R is —CHO and R$_3$ is —CH$_2$SO$_2$R$_5$, the reaction of the compound of Formula 2 and the compound of Formula 3 may be carried out using lithium bis(trimethylsilyl)amide, sodium bis(trimethylsilyl)amide, or potassium bis(trimethylsilyl)amide as a base; and tetrahydrofuran, dimethoxyethane, or toluene as a solvent. The reaction may be performed at a temperature ranging –90~20° C., preferably –70~0° C.

The present invention also provides the following compound of Formula 3 useful for preparing the compound of Formula 4:

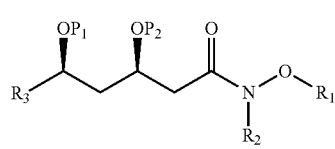

<Formula 3> wherein, R$_1$, R$_2$, P$_1$ and P$_2$ are the same as defined in the above, and R$_3$ is —CH$_2$SO$_2$R$_5$ (wherein, R$_5$ is the same as defined in the above). In the compound of Formula 3, the following compound of Formula 3a is more preferable.

<Formula 3a>

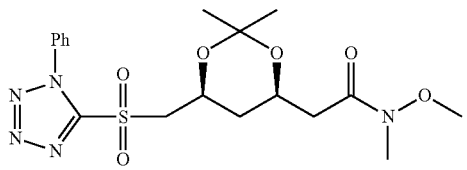

wherein, Ph is phenyl.

The following examples are intended to further illustrate the present invention without limiting its scope of the present invention.

Preparation 1

N-[4-(4-fluorophenyl)-5-hydroxymethyl-6-isopropyl-pyrimidin-2-yl]-N-methyl-methanesulfonamide Ethyl 2-(N-methyl-N-methanesulfonylamino)-4-(4-fluorophenyl)-6-isopropyl-pyrimidin-5-carboxylic acid (100.0 g) and toluene (500.0 mL) were added to a reactor under nitrogen atmosphere. The reaction mixture was cooled to −78° C. A solution of diisobutylaluminium hydride in toluene (1.5 M, 200.0 mL) was slowly added thereto. The temperature of the reaction mixture was adjusted to 0° C. The reaction mixture was stirred for over 1 hour and then water (500.0 mL) was added thereto. The separated organic layer was sequentially washed with 1N hydrochloric acid solution (500.0 mL), 5% sodium bicarbonate solution (500.0 mL), and then water (500.0 mL), and then concentrated under reduced pressure. n-Hexane (300.0 mL) was added to the resulting residue under stirring. The resulting suspension was filtered under reduced pressure, and then dried to obtain N-[4-(4-fluorophenyl)-5-hydroxymethyl-6-isopropyl-pyrimidin-2-yl]-N-methyl-methanesulfonamide as a white solid (72.3 g, yield 81%).

$^1$H-NMR, 400 MHz, CDCl$_3$, ppm: 1.31 (d, 6H), 3.47 (m, 1H), 3.50 (s, 3H), 3.57 (s, 3H), 4.63 (q, 2H), 7.15 (t, 2H), 7.80 (q, 2H)

Preparation 2

N-[5-chloromethyl-4-(4-fluorophenyl)-6-isopropyl-pyrimidin-2-yl]-N-methyl-methanesulfonamide N-[4-(4-fluorophenyl)-5-hydroxymethyl-6-isopropyl-pyrimidin-2-yl]-N-methyl-methanesulfonamide (50.0 g), dichloromethane (250.0 mL), and triethylamine (47.3 mL) were added to a reactor and then the reaction mixture was cooled to 0~5° C. Methanesulfonyl chloride (13.2 mL) was slowly added to the reaction mixture, which was then stirred at 20~25° C. for 5 hours. Water (100.0 mL) was added to the reaction mixture. The separated organic layer was sequentially washed with 0.5N hydrochloric acid solution (100.0 mL) and then water (100.0 mL). The organic layer was concentrated under reduced pressure to remove the solvent. n-Hexane (150.0 mL) was added to the resulting residue under stirring. The resulting suspension was filtered under reduced pressure. The resulting white solid was dried to obtain N-[5-chloromethyl-4-(4-fluorophenyl)-6-isopropyl-pyrimidin-2-yl]-N-methyl-methanesulfonamide (45.5 g, yield 88%).

$^1$H-NMR, 400 MHz, CDCl$_3$, ppm: 1.35 (d, 6H), 3.48 (m, 1H), 3.50 (s, 3H), 3.57 (s, 3H), 4.58 (q, 2H), 7.22 (t, 2H), 7.80 (q, 2H)

Preparation 3

N-[5-bromomethyl-4-(4-fluorophenyl)-6-isopropyl-pyrimidin-2-yl]-N-methyl-methanesulfonamide N-[4-(4-fluorophenyl)-5-hydroxymethyl-6-isopropyl-pyrimidin-2-yl]-N-methyl-methanesulfonamide (50.0 g) and 48% hydrogen bromide (130.0 mL) were added to a reactor. The reaction mixture was stirred at 80° C. for 15 hours. The reaction was monitored with thin layer chromatography (ethyl acetate/n-hexane=1:2). The reaction mixture was cooled to 20~25° C., stirred for over 1 hour, and then filtered under reduced pressure. The resulting white solid was washed with water (500.0 mL) and then dried under reduced pressure to obtain N-[5-bromomethyl-4-(4-fluorophenyl)-6-isopropyl-pyrimidin-2-yl]-N-methyl-methanesulfonamide as a white solid (55.3 g, yield 94%).

$^1$H-NMR, 400 MHz, CDCl$_3$, ppm: 1.35 (d, 6H), 3.48 (m, 1H), 3.49 (s, 3H), 3.56 (s, 3H), 4.48 (q, 2H), 7.23 (t, 2H), 7.81 (q, 2H)

Preparation 4

Tributyl[2-(N-methyl-N-methanesulfonylamino)-4-(4-fluorophenyl)-6-isopropyl-pyrimidin-5-ylmethyl]phosphonium bromide N-[5-bromomethyl-4-(4-fluorophenyl)-6-isopropyl-pyrimidin-2-yl]-N-methyl-methanesulfonamide (55.3 g) and toluene (500.0 mL) were added to a reactor. The reaction mixture was cooled to 0~5° C. and then tributylphosphine (35.0 mL) was added thereto. The temperature of the reaction mixture was raised to 10~20° C. The reaction mixture was stirred at the same temperature for 3 hours and then filtered under reduced pressure. The resulting white solid was washed with toluene (331.0 mL) and then dried under reduced pressure to obtain tributyl[2-(N-methyl-N-methanesulfonylamino)-4-(4-fluorophenyl)-6-isopropyl-pyrimidin-5-ylmethyl]phosphonium bromide as a white solid (80.1 g, yield 97.6%).

$^1$H-NMR, 400 MHz, CDCl$_3$, ppm: 0.87 (t, 9H), 1.16 (m, 6H), 1.13 (m, 12H), 2.14 (m, 6H), 3.48 (s, 3H), 3.57 (s, 3H), 3.69 (m, 1H), 4.72 (s, 2H), 7.16 (t, 2H), 7.72 (q, 2H)

Preparation 5

Diphenyl[2-(N-methyl-N-methanesulfonylamino)-4-(4-fluorophenyl)-6-isopropyl-pyrimidin-5-ylmethyl]phosphine oxide N-[5-bromomethyl-4-(4-fluorophenyl)-6-isopropyl-pyrimidin-2-yl]-N-methyl-methanesulfonamide (10.0 g), toluene (100.0 mL), and diphenyl(ethoxy)phosphorane (6.2 g) were added to a reactor. The reaction mixture was stirred at 90~100° C. for 9 hours and then water (80.0 mL) was added thereto. The separated organic layer was concentrated under reduced pressure. The resulting residue was purified with silica gel column chromatography (ethyl acetate/n-hexane=1:1) to obtain diphenyl[2-(N-methyl-N-methanesulfonylamino)-4-(4-fluorophenyl)-6-isopropyl-pyrimidin-5-ylmethyl]phosphine oxide as a white solid (9.4 g, yield 73%).

$^1$H-NMR, 400 MHz, CDCl$_3$, ppm: 1.26 (d, 6H), 3.41 (m, 1H), 3.46 (s, 3H), 3.51 (s, 3H), 3.92 (d, 2H), 6.95 (m, 2H), 7.12 (t, 2H), 7.57 (m, 12H)

Preparation 6

N-[5-benzothiazol-2-sulfonylmethyl-4-(4-fluorophenyl)-6-isopropyl-pyrimidin-2-yl]-N-methyl-methanesulfonamide 2-Mercaptobenzothiazole (4.1 g) was added to a solution of sodium hydroxide (1.0 g) in water (20.0 mL). The reaction mixture was stirred for 15 minutes, while maintaining the temperature of 25~35° C. Acetone (36.0 mL) and N-[5-chloromethyl-4-(4-fluorophenyl)-6-isopropyl-pyrimidin-2-yl]-N-methyl-methanesulfonamide (9.0 g) were added to the reaction mixture, which was then stirred for 3 hours, while maintaining the temperature of 25~35° C. The reaction was monitored with thin layer chromatography (ethyl acetate/n-hexane=1:3). The reaction mixture was cooled to 20~25° C. and then water (45.0 mL) was added thereto. The separated organic layer was concentrated under reduced pressure to remove the solvent. Dichloromethane (90.0 mL) was added to the resulting residue, which was then cooled to 0~5° C. m-Chloroperbenzoic acid (13.5 g) was added to the reaction mixture, which was then stirred at 0~5° C. for 2 hours. The reaction was monitored with thin layer chromatography (ethyl acetate/n-hexane=1:3). The temperature of the reaction mixture was adjusted to 20~25° C. 10% Sodium sulfite solution (90.0 mL) was added to the reaction mixture under stirring. The separated organic layer was sequentially washed with 8% sodium bicarbonate solution (90.0 mL) and water (90.0 mL), and then concentrated under reduced pressure to remove the solvent. The resulting residue was purified with silica gel column chromatography (ethyl acetate/n-hexane=1:3) to obtain N-[5-benzothiazol-2-sulfonylmethyl-4-(4-fluorophenyl)-6-isopropyl-pyrimidin-2-yl]-N-methyl-methanesulfonamide as a white solid (10.9 g, yield 84%).

$^1$H-NMR, 400 MHz, CDCl$_3$, ppm: 1.35 (d, 6H), 3.48 (s, 3H), 3.55 (s, 3H), 3.59 (m, 1H), 5.06 (s, 2H), 6.79 (t, 2H), 7.25 (m, 2H), 7.63 (q, 2H), 7.96 (d, 1H), 8.07 (d, 1H)

Preparation 7

[(4R,6S)-6-hydroxymethyl-2,2-dimethyl-[1,3]dioxan-4-yl]-acetic acid tert-Butyl-2-[(4R,6S)-6-hydroxymethyl-2,2-dimethyl-[1,3]dioxan-4-yl]acetate (100.0 g), methanol (700.0 mL), water (100.0 mL), and sodium hydroxide (30.7 g) were added to a reactor. The reaction mixture was stirred at 40~50° C. for over 8 hours. The reaction was monitored with thin layer chromatography (ethyl acetate/n-hexane=1:1). The reaction mixture was cooled to 15~20° C. and then the pH of the reaction mixture was adjusted to 4.0~4.2 using 6N hydrochloric acid solution. The reaction mixture was concentrated under reduced pressure to remove the solvent. Ethyl acetate (800.0 mL) and sodium sulfate (100.0 g) were added to the resulting residue, which was then stirred for over 1 hour. The resulting suspension was filtered under reduced pressure. The filtrate was washed with ethyl acetate (200.0 mL) and then concentrated under reduced pressure to obtain [(4R,6S)-6-hydroxymethyl-2,2-dimethyl-[1,3]dioxan-4-yl]-acetic acid (80.0 g, yield 102%) as a gel form.

$^1$H-NMR, 400 MHz, CDCl$_3$, ppm: 1.33~1.56 (m, 2H), 1.36 (s, 3H), 1.48 (s, 3H), 2.46~2.57 (m, 2H), 3.50~3.65 (m, 2H), 4.02 (m, 1H), 4.34 (m, 1H)

Preparation 8

[(4R,6S)-6-methanesulfonyloxymethyl-2,2-dimethyl-[1,3]dioxan-4-yl]-acetic acid tert-Butyl-2-[(4R,6S)-6-hydroxymethyl-2,2-dimethyl-[1,3]dioxan-4-yl]acetate (10.0 g) and dichloromethane (60.0 mL) were added to a reactor. The reaction mixture was cooled to 0~5° C. Triethylamine (12.9 mL) and methanesulfonyl chloride (3.6 mL) was added to the reaction mixture, which was then stirred at 0~5° C. for 1 hour. Water (500.0 mL) was added to the reaction mixture under stirring. The separated organic layer was concentrated under reduced pressure. Methanol (40.0 mL), water (20.0 mL), and sodium hydroxide (3.4 g) were added to the resulting residue. The reaction mixture was stirred at 40° C. for over 12 hours and then concentrated under reduced pressure. Water (30.0 mL) and ethyl acetate (60.0 mL) were added to the resulting residue and then the pH of the reaction mixture was adjusted to 2.0~4.0 using 6N hydrochloric acid solution. The separated organic layer was concentrated under reduced pressure to obtain [(4R,6S)-6-methanesulfonyloxymethyl-2,2-dimethyl-[1,3]dioxan-4-yl]-acetic acid as a gel form (10.0 g, yield 92%).

$^1$H-NMR, 400 MHz, CDCl$_3$, ppm: 1.34 (m, 1H), 1.39 (s, 3H), 1.47 (s, 3H), 1.63 (d, 1H), 2.47 (dd, 1H), 2.61 (dd, 1H), 3.01 (s, 3H), 4.18~4.21 (m, 3H), 4.36 (m, 1H)

Preparation 9

2-[(4R,6S)-6-methanesulfonyloxymethyl-2,2-dimethyl-[1,3]dioxan-4-yl]-N-methoxy-N-methyl-acetamide Ethyl acetate (50.0 mL) was added to [(4R,6S)-6-methanesulfonyloxymethyl-2,2-dimethyl-[1,3]dioxan-4-yl]-acetic acid (10.0 g) prepared in Preparation 8. The reaction mixture was cooled to 0~5° C. and then 1,1'-carbonyldiimidazole (7.6 g) was slowly added thereto. The temperature of the reaction mixture was raised to 20~30° C. The reaction mixture was stirred for 3 hours. Dimethylhydroxyamine hydrochloride (5.6 g) and sodium bicarbonate (3.2 g) were added to the reaction mixture, which was then stirred for over 3 hours while maintaining the temperature of 20~25° C. Water (40.0 mL) was added to the reaction mixture under stirring. The separated organic layer was concentrated under reduced pressure to obtain 2-[(4R,6S)-6-methanesulfonyloxymethyl-2,2-dimethyl-[1,3]dioxan-4-yl]-N-methoxy-N-methyl-acetamide (10.0 g, yield 87%).

$^1$H-NMR, 400 MHz, CDCl$_3$, ppm: 1.31 (m, 1H), 1.38 (s, 3H), 1.48 (s, 3H), 1.67 (d, 1H), 2.44 (dd, 1H), 2.79 (dd, 1H), 3.06 (s, 3H), 3.37 (s, 3H), 3.69 (s, 3H), 4.10~4.30 (m, 3H), 4.40 (m, 1H)

Example 1

2-[(4R,6S)-6-hydroxymethyl-2,2-dimethyl-[1,3]dioxan-4-yl]-N-methoxy-N-methyl-acetamide

[(4R,6S)-6-hydroxymethyl-2,2-dimethyl-[1,3]dioxan-4-yl]-acetic acid (50.0 g), acetonitrile (500.0 mL), and ammonium chloride (1.3 g) were added to a reactor. The reaction mixture was cooled to 0~5° C. and then hexamethyldisilazane (102.1 mL) was slowly added thereto. The reaction mixture was stirred at 30° C. for 1 hour and then concentrated under reduced pressure to remove the solvent. Ethyl acetate (250.0 mL) and water (200.0 mL) were added to the resulting residue. The separated organic layer was dehydrated with anhydrous magnesium sulfate (50.0 g) and then filtered under reduced pressure. The filtrate was concentrated under reduced pressure to obtain a concentrated residue in a colorless clear oil form. Dichloromethane (250.0 mL) was added to the concentrated residue. The reaction mixture was cooled to 0~5° C. and then 1,1'-carbonyldiimidazole (43.7 g) was slowly added thereto. The temperature of the reaction mixture was raised to 20~25° C. The reaction mixture was stirred at the same temperature for 3 hours and then N,O-dimethylhydroxyamine hydrochloride (26.4 g) and sodium bicarbonate (22.6 g) were added thereto. The reaction mixture was stirred for over 10 hours, while maintaining the temperature of 20~25° C. Water (250.0 mL) was added to the reaction mixture and then the resulting organic layer was separated. The water layer was extracted with dichloromethane (150.0 mL) to obtain an organic layer. The combined organic layer was dehydrated with anhydrous sodium sulfate (50.0 g) and then filtered under reduced pressure. The filtrate was concentrated under reduced pressure to remove the solvent, and then purified with silica gel column chromatography (ethyl acetate/n-hexane=1:4) to obtain 2-[(4R,6S)-6-hydroxymethyl-2,2-dimethyl-[1,3]dioxan-4-yl]-N-methoxy-N-methyl-acetamide in a colorless gel form (49.7 g, yield 82%).

$^1$H-NMR, 400 MHz, CDCl$_3$, ppm: 1.34 (m, 1H), 1.44 (s, 3H), 1.58 (s, 3H), 1.60 (d, 1H), 2.44~2.82 (dd, 2H), 3.29 (s, 3H), 3.47~3.64 (dd, 2H), 3.69 (s, 3H), 4.07 (m, 1H), 4.44 (m, 1H)

Example 2

2-[(4R,6S)-6-formyl-2,2-dimethyl-[1,3]dioxan-4-yl]-N-methoxy-N-methyl-acetamide 2-[(4R,6S)-6-hydroxymethyl-2,2-dimethyl-[1,3]dioxan-4-yl]-N-methoxy-N-methyl-acetamide (5.0 g), dichloromethane (30.0 mL), and Dess-Martin periodinane (11.2 g) were added to a reactor under nitrogen atmosphere. The reaction mixture was stirred at 20~30° C. for over 5 hours. Water (30.0 mL) was added to the reaction mixture. The separated organic layer was concentrated under reduced pressure. The resulting residue was purified with silica gel column chromatography (ethyl acetate/n-hexane=1:3) to obtain 2-[(4R,6S)-6-formyl-2,2-dimethyl-[1,3]dioxan-4-yl]-N-methoxy-N-methyl-acetamide as a white solid (4.3 g, yield 87%).

$^1$H-NMR, 400 MHz, CDCl$_3$, ppm: 1.30 (m, 1H), 1.46 (s, 3H), 1.51 (s, 3H), 1.92 (d, 1H), 2.42~2.83 (dd, 2H), 3.19 (s, 3H), 3.69 (s, 3H), 4.37 (d, 1H), 4.48 (m, 1H), 9.58 (s, 1H)

Example 3

2-[(4R,6S)-6-formyl-2,2-dimethyl-[1,3]dioxan-4-yl]-N-methoxy-N-methyl-acetamide 2-[(4R,6S)-6-hydroxymethyl-2,2-dimethyl-[1,3]dioxan-4-yl]-N-methoxy-N-methyl-acetamide (30.0 g), ethyl acetate (240.0 mL), sodium bicarbonate (28.5 g), potassium bromide (3.0 g), and TEMPO (0.06 g) were added to a reactor. The temperature of the reaction mixture was adjusted to 0~5° C. 10% Sodium hypochlorite solution (96.0 mL) was slowly added to the reaction mixture, which was then stirred at 0~5° C. for 2 hours. 5% Sodium sulfite solution (150.0 mL) was added to the reaction mixture. The separated organic layer was washed with 10% sodium chloride solution (150.0 mL). The organic layer was concentrated under reduced pressure to obtain 2-[(4R,6S)-6-formyl-2,2-dimethyl-[1,3]dioxan-4-yl]-N-methoxy-N-methyl-acetamide as a light brown solid (27.7 g, yield 93%).

$^1$H-NMR, 400 MHz, CDCl$_3$, ppm: 1.30 (m, 1H), 1.46 (s, 3H), 1.51 (s, 3H), 1.92 (d, 1H), 2.42~2.83 (dd, 2H), 3.19 (s, 3H), 3.69 (s, 3H), 4.37 (d, 1H), 4.48 (m, 1H), 9.58 (s, 1H)

Example 4

2-[(4R,6S)-2,2-dimethyl-6-(1-phenyl-1H-tetrazole-5-sulfonylmethyl)-[1,3]dioxan-4-yl]-N-methoxy-N-methyl-acetamide 2-[(4R,6S)-6-hydroxymethyl-2,2-dimethyl-[1,3]dioxan-4-yl]-N-methoxy-N-methyl-acetamide (10.0 g), dichloromethane (150.0 mL), and triethylamine (17.0 mL) were added to a reactor. Methanesulfonyl chloride (4.7 mL) was added to the reaction mixture, which was then stirred for 2 hours. Water (200.0 mL) was added to the reaction mixture under stirring. The separated organic layer was washed with 0.5N hydrochloric acid solution (100.0 mL) and then concentrated under reduced pressure to obtain 2-[(4R,6S)-6-methanesulfonyloxymethyl-2,2-dimethyl-[1,3]dioxan-4-yl]-N-methoxy-N-methyl-acetamide (13 g).

2-[(4R,6S)-6-methanesulfonyloxymethyl-2,2-dimethyl-[1,3]dioxan-4-yl]-N-methoxy-N-methyl-acetamide (6.0 g), dimethylformamide (150.0 mL), potassium carbonate (10.0 g), and 1-phenyl-tetrazole-5-thiol (3.5 g) were added to a reactor. The reaction mixture was heated to 70° C. and then stirred overnight. Toluene (150.0 mL) and water (150.0 mL) were added to the reaction mixture under stirring. The separated organic layer was concentrated under reduced pressure. Dichloromethane (100 mL) was added to the resulting residue and then m-chloroperbenzoic acid (4.1 g) was added thereto. The reaction mixture was stirred at 20~25° C. overnight and then 10% sodium sulfite solution (100 mL) was added thereto under stirring. 8% Sodium bicarbonate solution (100.0 mL) was added to the separated organic layer under stirring. The reaction mixture was concentrated under reduced pressure to obtain 2-[(4R,6S)-2,2-dimethyl-6-(1-phenyl-1H-tetrazole-5-sulfonylmethyl)-[1,3]dioxan-4-yl]-N-methoxy-N-methyl-acetamide as a solid (6.5 g, yield 79%).

$^1$H-NMR, 400 MHz, CDCl$_3$, ppm: 1.10 (s, 3H), 1.28 (q, 1H), 1.47 (s, 3H), 1.76 (d, 1H), 2.39~2.78 (dd, 2H), 3.18 (s, 3H), 3.16~3.44 (dd, 2H), 3.69 (s, 3H), 4.35 (m, 1H), 4.58 (t, 1H), 7.62 (s, 5H)

Example 5

2-[(4R,6S)-2,2-dimethyl-6-(1-phenyl-1H-tetrazole-5-sulfonylmethyl)-[1,3]dioxan-4-yl]-N-methoxy-N-methyl-acetamide 2-[(4R,6S)-6-hydroxymethyl-2,2-dimethyl-[1,3]dioxan-4-yl]-N-methoxy-N-methyl-acetamide (100.0 g), dichloromethane (800.0 mL), and triethylamine (160.6 mL) were added to a reactor. The reaction mixture was then cooled to 0~5° C. and then methanesulfonyl chloride (44.6 mL) was added thereto, while maintaining the temperature of 0~10° C. The reaction mixture was stirred at the same temperature for 2 hours and then water (500.0 mL) was added thereto. The separated organic layer was washed with 0.5N hydrochloric acid solution (300.0 mL) and then concentrated under reduced pressure to obtain 2-[(4R,6S)-6-methanesulfonyloxymethyl-2,2-dimethyl-[1,3]dioxan-4-yl]-N-methoxy-N-methyl-acetamide (131 g).

2-[(4R,6S)-6-methanesulfonyloxymethyl-2,2-dimethyl-[1,3]dioxan-4-yl]-N-methoxy-N-methyl-acetamide (131 g), acetonitrile (786.0 mL), potassium carbonate (114.9 g), and 1-phenyl-tetrazole-5-thiol (107.6 g) were added to a reactor. The reaction mixture was heated to 70° C. and then stirred overnight. Toluene (786.0 mL) and water (655.0 mL) were added to the reaction mixture under stirring. The separated organic layer was concentrated under reduced pressure. Ethanol (1,310.0 mL) was added to the resulting residue. The reaction mixture was cooled to 0~5° C. and then a solution of ammonium molybdate tetrahydrate (39.7 g) in 10% hydrogen peroxide (430.0 mL) was slowly added thereto. The temperature of the reaction mixture was raised to 20~25° C. The reaction mixture was stirred at the same temperature for 15 hours. The reaction was monitored with thin layer chromatography (ethyl acetate/n-hexane=1:2). Water (655.0 mL) and ethyl acetate (786.0 mL) were added to the reaction mixture and then 10% sodium sulfite solution (1310.0 mL) was added thereto under stirring. 8% Sodium bicarbonate solution (655.0 mL) was added to the separated organic layer under stirring. The reaction mixture was concentrated under reduced pressure. Diisopropyl ether (655.0 mL) was added to the resulting residue. The reaction mixture was stirred at 20~25° C. for 2 hours and then filtered under reduced pressure to obtain 2-[(4R,6S)-2,2-dimethyl-6-(1-phenyl-1H-tetrazole-5-sulfonylmethyl)-[1,3]dioxan-4-yl]-N-methoxy-N-methyl-acetamide as a solid (163.5 g, yield 92%).

$^1$H-NMR, 400 MHz, CDCl$_3$, ppm: 1.10 (s, 3H), 1.28 (q, 1H), 1.47 (s, 3H), 1.76 (d, 1H), 2.39~2.78 (dd, 2H), 3.18 (s, 3H), 3.16~3.44 (dd, 2H), 3.69 (s, 3H), 4.35 (m, 1H), 4.58 (t, 1H), 7.62 (s, 5H)

Example 6

2-[(4R,6S)-2,2-dimethyl-6-(1-phenyl-1H-tetrazole-5-sulfonylmethyl)-[1,3]dioxan-4-yl]-N-methoxy-N-methyl-acetamide 2-[(4R,6S)-6-methanesulfonyloxymethyl-2,2-dimethyl-[1,3]dioxan-4-yl]N-methoxy-N-methyl-acetamide (10.0 g) prepared in Preparation 9, acetonitrile (100.0 mL), dimethylformamide (10.0 mL), potassium carbonate (8.5 g), and 1-phenyl-tetrazole-5-thiol (11.0 g) were added to a reactor. The reaction mixture was stirred at 70° C. overnight and then toluene (70.0 mL) and water (50.0 mL) were added thereto. The separated organic layer was washed with 10% sodium carbonate solution (50.0 mL) and water (50.0 mL), and then concentrated under reduced pressure. Ethanol (104.0 mL) was added to the resulting residue. The reaction mixture was cooled to 0~5° C. 30% Hydrogen peroxide (31.8 mL) and ammonium molybdate tetrahydrate (3.2 g) were added to the reaction mixture, which was then stirred at 20~30° C. for over 20 hours. 10% Sodium sulfite solution (200.0 mL) and water (52.0 mL) were added to the reaction mixture for crystallization. The reaction mixture was filtered under reduced pressure. The resulting solid was dried under vacuum to obtain 2-[(4R,6S)-2,2-dimethyl-6-(1-phenyl-1H-tetrazole-5-sulfonylmethyl)-[1,3]dioxan-4-yl]-N-methoxy-N-methyl-acetamide (11.0 g, yield 83%).

$^1$H-NMR, 400 MHz, CDCl$_3$, ppm: 1.10 (s, 3H), 1.28 (q, 1H), 1.47 (s, 3H), 1.76 (d, 1H), 2.39~2.78 (dd, 2H), 3.18 (s, 3H), 3.16~3.44 (dd, 2H), 3.69 (s, 3H), 4.35 (m, 1H), 4.58 (t, 1H), 7.62 (s, 5H)

Example 7

E-(6-{2-[2-(N-methyl-N-methanesulfonylamino)-4-(4-fluorophenyl)-6-isopropyl-pyrimidin-5-yl]vinyl}-[(4R,6S)-2,2-dimethyl-[1,3]dioxan-4-yl])-N-methoxy-N-methyl-acetamide Tributyl[2-(N-methyl-N-methanesulfonylamino)-4-(4-fluorophenyl)-6-isopropyl-pyrimidin-5-ylmethyl]phosphonium bromide (13.9 g), 2-[(4R,6S)-6-formyl-2,2-dimethyl-[1,3]dioxan-4-yl]-N-methoxy-N-methyl-acetamide (5.0 g), dimethylformamide (100.0 mL), and potassium carbonate (8.5 g) were added to a reactor. The reaction mixture was stirred at 70~75° C. for 6 hours. The reaction was monitored with thin layer chromatography (ethyl acetate/n-hexane=1:3). The reaction mixture was cooled to 20~30° C. Water (60.0 mL) was added to the reaction mixture under stirring. The separated organic layer was washed with water (60.0 mL) and 2% sodium chloride solution (50.0 mL). The organic layer was concentrated under reduced pressure to remove the solvent and then isopropanol (50.0 mL) was added thereto. The reaction mixture was stirred at 0~5° C. for over 1 hour and then filtered under reduced pressure. The resulting white solid was dried under vacuum to obtain E-(6-{2-[2-(N-methyl-N-methanesulfonylamino)-4-(4-fluorophenyl)-6-isopropyl-pyrimidin-5-yl]vinyl}-[(4R,6S)-2,2-dimethyl-[1,3]dioxan-4-yl])-N-methoxy-N-methyl-acetamide (8.8 g, yield 76%).

$^1$H-NMR, 400 MHz, CDCl$_3$, ppm: 1.23~1.27 (m, 7H), 1.40 (s, 3H), 1.50 (s, 3H), 2.42~2.80 (dd, 2H), 3.20 (s, 3H), 3.37 (q, 1H), 3.51 (s, 3H), 3.57 (s, 3H), 3.70 (s, 3H), 4.41 (m, 2H), 5.44 (dd, 1H), 6.49 (d, 2H), 7.08 (t, 2H), 7.64 (q, 2H)

Example 8

E-(6-{2-[2-(N-methyl-N-methanesulfonylamino)-4-(4-fluorophenyl)-6-isopropyl-pyrimidin-5-yl]vinyl}-[(4R,6S)-2,2-dimethyl-[1,3]dioxan-4-yl])-N-methoxy-N-methyl-acetamide Diphenyl[2-(N-methyl-N-methanesulfonylamino)-4-(4-fluorophenyl)-6-isopropyl-pyrimidin-5-ylmethyl]phosphine oxide (10.9 g), 2-[(4R,6S)-6-formyl-2,2-dimethyl-[1,3]dioxan-4-yl]-N-methoxy-N-methyl-acetamide (4.5 g), and tetrahydrofuran (90.0 mL) were added to a reactor under nitrogen atmosphere. The reaction mixture was cooled to −40~−30° C. A solution of sodium bis(trimethylsilyl)amide in tetrahydrofuran (1M, 20.0 mL) was slowly added to the reaction mixture, while maintaining the temperature of −40~−30° C. The temperature of the reaction mixture was raised to 0~5° C. for 30 minutes. The reaction mixture was stirred at the same temperature for 2~3 hours. The reaction was monitored with thin layer chromatography (ethyl acetate/n-hexane=1:3). An ammonium chloride solution (50.0 mL) was added to the reaction mixture. The separated organic layer was washed with 8% sodium bicarbonate solution (50.0 mL) and then concentrated under reduced pressure. Isopropanol (45.0 mL) was added to the resulting residue. The reaction mixture was stirred at 0~5° C. for 1~2 hours and then filtered under reduced pressure. The resulting white solid was dried under vacuum to obtain E-(6-{2-[2-(N-methyl-N-methanesulfonylamino)-4-(4-fluorophenyl)-6-isopropyl-pyrimidin-5-yl]vinyl}-[(4R,6S)-2,2-dimethyl-[1,3]dioxan-4-yl])-N-methoxy-N-methyl-acetamide (7.8 g, yield 75%).

$^1$H-NMR, 400 MHz, CDCl$_3$, ppm: 1.23~1.27 (m, 7H), 1.40 (s, 3H), 1.50 (s, 3H), 2.42~2.80 (dd, 2H), 3.20 (s, 3H), 3.37 (q, 1H), 3.51 (s, 3H), 3.57 (s, 3H), 3.70 (s, 3H), 4.41 (m, 2H), 5.44 (dd, 1H), 6.49 (d, 2H), 7.08 (t, 2H), 7.64 (q, 2H)

Example 9

E-(6-{2-[2-(N-methyl-N-methanesulfonylamino)-4-(4-fluorophenyl)-6-isopropyl-pyrimidin-5-yl]vinyl}-[(4R,6S)-2,2-dimethyl-[1,3]dioxan-4-yl])-N-methoxy-N-methyl-acetamide N-[5-benzothiazol-2-sulfonylmethyl-4-(4-fluorophenyl)-6-isopropyl-pyrimidin-2-yl]-N-methyl-methanesulfonamide (10.0 g), 2-[(4R,6S)-6-formyl-2,2-dimethyl-[1,3]dioxan-4-yl]-N-methoxy-N-methyl-acetamide (4.6 g), and tetrahydrofuran (92.0 mL) were added to a reactor under nitrogen atmosphere. The reaction mixture was cooled to −40~−30° C. A solution of sodium bis(trimethylsilyl)amide in tetrahydrofuran (1M, 20.0 mL) was slowly added to the reaction mixture, while maintaining the temperature of −40~−30° C. The temperature of the reaction mixture was raised to 0~5° C. for 30 minutes. The reaction mixture was stirred at the same temperature for 2~3 hours. The reaction was monitored with thin layer chromatography (ethyl acetate/n-hexane=1:3). An ammonium chloride solution (50.0 mL) was added to the reaction mixture. The separated organic layer was washed with 8% sodium bicarbonate solution (50.0 mL) and then concentrated under reduced pressure. Isopropanol (46.0 mL) was added to the resulting residue. The reaction mixture was stirred at 0~5° C. for 1~2 hours and then filtered under reduced pressure. The resulting white solid was dried under vacuum to obtain E-(6-{2-[2-(N-methyl-N-methanesulfonylamino)-4-(4-fluorophenyl)-6-isopropyl-pyrimidin-5-yl]vinyl}-[(4R,6S)-2,2-dimethyl-[1,3]dioxan-4-y]D-N-methoxy-N-methyl-acetamide (7.7 g, yield 72%).

$^1$H-NMR, 400 MHz, CDCl$_3$, ppm: 1.23~1.27 (m, 7H), 1.40 (s, 3H), 1.50 (s, 3H), 2.42~2.80 (dd, 2H), 3.20 (s, 3H), 3.37 (q, 1H), 3.51 (s, 3H), 3.57 (s, 3H), 3.70 (s, 3H), 4.41 (m, 2H), 5.44 (dd, 1H), 6.49 (d, 2H), 7.08 (t, 2H), 7.64 (q, 2H)

Example 10

E-(6-{2-[2-(N-methyl-N-methanesulfonylamino)-4-(4-fluorophenyl)-6-isopropyl-pyrimidin-5-yl]vinyl}-[(4R,6S)-2,2-dimethyl-[1,3]dioxan-4-yl])-N-methoxy-N-methyl-acetamide 2-[(4R,6S)-2,2-dimethyl-6-(1-phenyl-1H-tetrazole-5-sulfonylmethyl)-[1,3]dioxan-4-yl]-N-methoxy-N-methyl-acetamide (5.4 g), N-[4-(4-fluorophenyl)-5-formyl-6-isopropyl-pyrimidin-2-yl]-N-methyl-methanesulfonamide (3.9 g), and tetrahydrofuran (54 mL) were added to a reactor and then the reaction mixture was cooled to −70° C. A solution of lithium bis(trimethylsilyl)amide in tetrahydrofuran (1M, 15.0 mL) was slowly added to the reaction mixture, the temperature of which was then adjusted to −20~−10° C. The reaction mixture was stirred for 1 hours and then 8% sodium bicarbonate solution (100.0 mL) was added under stirring. The separated organic layer was washed with water (100.0 mL) and then concentrated under reduced pressure to obtain E-(6-{2-[2-(N-methyl-N-methanesulfonylamino)-4-(4-fluorophenyl)-6-isopropyl-pyrimidin-5-yl]vinyl}-[(4R,6S)-2,2-dimethyl-[1,3]dioxan-4-y]D-N-meth oxy-N-methyl-acetamide as a solid (5 g, yield 80%).

$^1$H-NMR, 400 MHz, CDCl$_3$, ppm: 1.23~1.27 (m, 7H), 1.40 (s, 3H), 1.50 (s, 3H), 2.42~2.80 (dd, 2H), 3.20 (s, 3H), 3.37 (q, 1H), 3.51 (s, 3H), 3.57 (s, 3H), 3.70 (s, 3H), 4.41 (m, 2H), 5.44 (dd, 1H), 6.49 (d, 2H), 7.08 (t, 2H), 7.64 (q, 2H)

Example 11

E-6-{2-[2-(N-methyl-N-methanesulfonylamino)-4-(4-fluorophenyl)-6-isopropyl-pyrimidin-5-yl]vinyl}-(4R,6S)-4-hydroxy-3,4,5,6-tetrahydro-2H-pyran-2-one (compound of Formula 5)

E-(6-{2-[2-(N-methyl-N-methanesulfonylamino)-4-(4-fluorophenyl)-6-isopropyl-pyrimidin-5-yl]vinyl}-[(4R,6S)-2,2-dimethyl-[1,3]dioxan-4-yl])-N-methoxy-N-methyl-acetamide (5.0 g), acetonitrile (30.0 mL), and sulfuric acid (0.47 mL) were added to a reactor and then the reaction mixture was stirred at 50~60° C. for 3 hours. The reaction mixture was concentrated under reduced pressure and then ethyl acetate (30.0 mL) and water (30.0 mL) were added thereto. The separated organic layer was dried under reduced pressure to obtain E-6-{2-[2-(N-methyl-N-methanesulfonylamino)-4-(4-fluorophenyl)-6-isopropyl-pyrimidin-5-yl]vinyl}-(4R,6S)-4-hydroxy-3,4,5,6-tetrahydro-2H-pyran-2-one (3.4 g, yield 82%).

$^1$H-NMR, 400 MHz, CDCl$_3$, ppm: 1.27 (m, 6H), 1.46 (m, 2H), 2.45 (d, 2H), 3.36 (m, 1H), 3.52 (s, 3H), 3.57 (s, 3H), 4.46 (m, 2H), 5.45 (dd, 1H), 6.66 (d, 1H), 7.08 (t, 2H), 7.65 (q, 2H)

Example 12

E-6-{2-[2-(N-methyl-N-methanesulfonylamino)-4-(4-fluorophenyl)-6-isopropyl-pyrimidin-5-yl]vinyl}-(4R,6S)-4-hydroxy-3,4,5,6-tetrahydro-2H-pyran-2-one (compound of Formula 5)

E-(6-{2-[2-(N-methyl-N-methanesulfonylamino)-4-(4-fluorophenyl)-6-isopropyl-pyrimidin-5-yl]vinyl}-[(4R,6S)-2,2-dimethyl-[1,3]dioxan-4-yl])-N-methoxy-N-methyl-acetamide (3.0 g), acetonitrile (20.0 mL), and hydrochloric acid (0.46 mL) were added to a reactor and then the reaction mixture was stirred at 50~60° C. for 5 hours. The reaction mixture was concentrated under reduced pressure and then ethyl acetate (20.0 mL) and water (20.0 mL) were added thereto. The separated organic layer was dried under reduced pressure to obtain E-6-{2-[2-(N-methyl-N-methanesulfonylamino)-4-(4-fluorophenyl)-6-isopropyl-pyrimidin-5-yl]vinyl}-(4R,6S)-4-hydroxy-3,4,5,6-tetrahydro-2H-pyran-2-one (1.6 g, yield 64%).

$^1$H-NMR, 400 MHz, CDCl$_3$, ppm: 1.27 (m, 6H), 1.46 (m, 2H), 2.45 (d, 2H), 3.36 (m, 1H), 3.52 (s, 3H), 3.57 (s, 3H), 4.46 (m, 2H), 5.45 (dd, 1H), 6.66 (d, 1H), 7.08 (t, 2H), 7.65 (q, 2H)

Example 13

E-6-{2-[2-(N-methyl-N-methanesulfonylamino)-4-(4-fluorophenyl)-6-isopropyl-pyrimidin-5-yl]vinyl}-(4R,6S)-4-hydroxy-3,4,5,6-tetrahydro-2H-pyran-2-one (compound of Formula 5)

E-(6-{2-[2-(N-methyl-N-methanesulfonylamino)-4-(4-fluorophenyl)-6-isopropyl-pyrimidin-5-yl]vinyl}-[(4R,6S)-2,2-dimethyl-[1,3]dioxan-4-yl])-N-methoxy-N-methyl-acetamide (4.0 g), acetonitrile (25.0 mL), and nitric acid (0.49 mL) were added to a reactor and then the reaction mixture was stirred at 50~60° C. for 3 hours. The reaction mixture was concentrated under reduced pressure and then ethyl acetate (25.0 mL) and water (25.0 mL) were added thereto. The separated organic layer was dried under reduced pressure to obtain E-6-{2-[2-(N-methyl-N-methanesulfonylamino)-4-(4-fluorophenyl)-6-isopropyl-pyrimidin-5-yl]vinyl}-(4R,6S)-4-hydroxy-3,4,5,6-tetrahydro-2H-pyran-2-one (1.9 g, yield 58%).

$^1$H-NMR, 400 MHz, CDCl$_3$, ppm: 1.27 (m, 6H), 1.46 (m, 2H), 2.45 (d, 2H), 3.36 (m, 1H), 3.52 (s, 3H), 3.57 (s, 3H), 4.46 (m, 2H), 5.45 (dd, 1H), 6.66 (d, 1H), 7.08 (t, 2H), 7.65 (q, 2H)

Example 14

E-7-[2-(N-methyl-N-methanesulfonylamino)-4-(4-fluorophenyl)-6-isopropyl-pyrimidin-5-yl]-(3R,5S)-3,5-dihydroxyhept-6-enoic acid 1/2 calcium salt (Rosuvastatin calcium, compound of Formula 1)

E-6-{2-[2-(N-methyl-N-methanesulfonylamino)-4-(4-fluorophenyl)-6-isopropyl-pyrimidin-5-yl]vinyl}-(4R,6S)-4-hydroxy-3,4,5,6-tetrahydro-2H-pyran-2-one (4.0 g), water (20.0 mL), and calcium hydroxide (0.64 g) was added to a reactor. The reaction mixture was stirred at room temperature for 3 hours and then filtered under reduced pressure. The resulting white solid was dried to obtain E-7-[2-(N-methyl-N-methanesulfonylamino)-4-(4-fluorophenyl)-6-isopropyl-pyrimidin-5-yl]-(3R,5S)-3,5-dihydroxyhept-6-enoic acid 1/2 calcium salt (4.1 g, yield 95%).

$^1$H-NMR, 400 MHz, CDCl$_3$, ppm: 1.27~1.49 (m, 2H), 1.90~2.09 (m, 2H), 3.44 (s, 3H), 3.54 (s, 3H), 3.69 (m, 1H), 4.20 (m, 1H), 5.03 (m, 1H), 5.51 (m, 1H), 6.51 (d, 1H), 7.30 (t, 2H), 7.73 (q, 2H)

Example 15

E-(7-{2-(N-methyl-N-methanesulfonylamino)-4-(4-fluorophenyl)-6-isopropyl-pyrimidin-5-yl}-[(3R,5S)-3,5-dihydroxy-hept-6-enoic acid])-N-methoxy-N-methyl-amide (compound of Formula 6)

E-(6-{2-[2-(N-methyl-N-methanesulfonylamino)-4-(4-fluorophenyl)-6-isopropyl-pyrimidin-5-yl]vinyl}-[(4R,6S)-2,2-dimethyl-[1,3]dioxan-4-yl])-N-methoxy-N-methyl-acetamide (43.4 g) and acetonitrile (300.0 mL) were added to a reactor and then the reaction mixture was heated to 40° C. 0.02N Hydrochloric acid solution (85.2 g) was added to the reaction mixture, which was stirred for 16 hours and then concentrated under reduced pressure. Dichloromethane (240.0 mL) and water (180.0 mL) were added to the resulting residue under stirring. The separated organic layer was concentrated under reduced pressure to obtain E-(7-{2-(N-methyl-N-methanesulfonylamino)-4-(4-fluorophenyl)-6-isopropyl-pyrimidin-5-yl}-[(3R,5S)-3,5-dihydroxy-hept-6-enoic acid])-N-methoxy-N-methyl-amide (38.0 g, yield 95%).

$^1$H-NMR, 400 MHz, CDCl$_3$, ppm: 1.27 (m, 6H), 1.46 (d, 1H), 1.57 (m, 1H), 2.50 (m, 1H), 2.62 (m, 1H), 3.20 (s, 3H), 3.52 (s, 3H), 3.57 (s, 3H), 3.69 (s, 3H), 3.90 (s, 1H), 4.25 (s, 1H), 4.41 (s, 1H), 4.48 (s, 1H), 5.48 (dd, 1H), 6.70 (d, 1H), 7.08 (t, 2H), 7.65 (q, 2H)

Example 16

E-7-[2-(N-methyl-N-methanesulfonylamino)-4-(4-fluorophenyl)-6-isopropyl-pyrimidin-5-yl]-(3R,5S)-3,5-dihydroxyhept-6-enoic acid diisopropylamine salt (compound of Formula 8)

E-(7-{2-(N-methyl-N-methanesulfonylamino)-4-(4-fluorophenyl)-6-isopropyl-pyrimidin-5-yl}-[(3R,5S)-3,5-dihydroxy-hept-6-enoic acid])-N-methoxy-N-methyl-amide (38.3 g), ethyl alcohol (300.0 mL), and a solution of sodium hydroxide (5.1 g) in water (60.0 mL) were added to a reactor. The reaction mixture was stirred for 16 hours while maintaining the temperature of 20~25° C., and then concentrated under reduced pressure. Ethyl acetate (240.0 mL) and water (360.0 mL) were added to the resulting residue under stirring. Ethyl acetate (240.0 mL) was added to the separated water layer, which was then adjusted to pH 3.0~4.0 using 1N hydrochloric acid solution. The separated organic layer was concentrated under reduced pressure. Tetrahydrofuran (900.0 mL) and diisopropylamine (12.0 mL) were added to the resulting residue. The reaction mixture was stirred at 20~25° C. for over 12 hours and then filtered under reduced pressure. The resulting white solid was dried under vacuum to obtain E-7-[2-(N-methyl-N-methanesulfonylamino)-4-(4-fluorophenyl)-6-isopropyl-pyrimidin-5-yl]-(3R,5S)-3,5-dihydroxyhept-6-enoic acid diisopropylamine salt (38.0 g, yield 90%, HPLC purity 99.7%).

$^1$H-NMR, 400 MHz, CDCl$_3$, ppm: 1.25 (d, 6H), 1.30 (m, 9H), 1.46 (m, 2H), 2.20 (m, 1H), 2.30 (d, 1H), 3.25 (m, 2H), 3.30 (d, 1H), 3.41 (s, 3H), 3.52 (s, 3H), 4.10 (t, 3H), 4.46 (d, 1H), 5.48 (dd, 1H), 6.60 (d, 1H), 7.05 (t, 2H), 7.68 (q, 2H)

Example 17

E-7-[2-(N-methyl-N-methanesulfonylamino)-4-(4-fluorophenyl)-6-isopropyl-pyrimidin-5-yl]-(3R,5S)-3,5-dihydroxyhept-6-enoic acid 1/2 calcium salt (Rosuvastatin calcium, compound of Formula 1)

A solution of E-7-[2-(N-methyl-N-methanesulfonylamino)-4-(4-fluorophenyl)-6-isopropyl-pyrimidin-5-yl]-(3R,5S)-3,5-dihydroxyhept-6-enoic acid diisopropylamine salt (40.0 g) in a mixed solvent of ethyl acetate (400.0 mL) and water (400.0 mL) was cooled to 0~5° C. The pH of the reaction mixture was adjusted to 3.0~4.0 using 1N hydrochloric acid solution. Water (360.0 mL) was added to the separated organic layer, the pH of which was then adjusted to 9.0~11.5 using 1N sodium hydroxide solution. Calcium chloride dihydrate (10.0 g) was added to the separated water layer. The reaction mixture was stirred at 20~25° C. for 2 hours and then filtered under reduced pressure. The resulting white solid was dried to obtain E-7-[2-(N-methyl-N-methanesulfonylamino)-4-(4-fluorophenyl)-6-isopropyl-pyrimidin-5-yl]-(3R,5S)-3,5-dihydroxyhept-6-enoic acid 1/2 calcium salt (33.0 g, yield 95%, HPLC purity 99.7%).

$^1$H-NMR, 400 MHz, CDCl$_3$, ppm: 1.27~1.49 (m, 2H), 1.90~2.09 (m, 2H), 3.44 (s, 3H), 3.54 (s, 3H), 3.69 (m, 1H), 4.20 (m, 1H), 5.03 (m, 1H), 5.51 (m, 1H), 6.51 (d, 1H), 7.30 (t, 2H), 7.73 (q, 2H)

Example 18

E-(6-{2-[3-(4-fluorophenyl)-1-isopropyl-1H-indol-2-yl]vinyl}-[(4R,6S)-2,2-dimethyl-[1,3]dioxan-4-yl])-N-methoxy-N-methyl-acetamide 2-[(4R,6S)-2,2-dimethyl-6-(1-phenyl-1H-tetrazole-5-sulfonylmethyl)-[1,3]dioxan-4-yl]-N-methoxy-N-methyl-acetamide (15.0 g), 3-(4-fluorophenyl)-1-isopropyl-1H-indol-2-carboxaldehyde (8.8 g), and tetrahydrofuran (350.0 mL) were added to a reactor and then the reaction mixture was cooled to −70° C. A solution of lithium bis(trimethylsilyl)amide in tetrahydrofuran (1M, 34.2 mL) was added to the reaction mixture, the temperature of which was adjusted to −20~−10° C. The reaction mixture was stirred at the same temperature for 1 hour and then 8% sodium bicarbonate solution (80.0 mL) was added thereto under stirring. The separated organic layer was washed with water (80.0 mL) and then concentrated under reduced pressure to obtain E-(6-{2-[3-(4-fluorophenyl)-1-isopropyl-1H-indol-2-yl]vinyl}-[(4R,6S)-2,2-dimethyl-[1,3]dioxan-4-y]D-N-methoxy-N-methyl-acetamide as a solid (13.1 g, yield 85%).

¹H-NMR, 400 MHz, CDCl₃, ppm: 1.12 (m, 1H), 1.42 (s, 3H), 1.52 (s, 3H), 1.59 (s, 1H), 1.65~1.67 (d, 6H), 2.47 (dd, 1H), 2.79 (dd, 1H), 3.20 (s, 3H), 3.70 (s, 3H), 4.40~4.50 (m, 2H), 4.85 (m, 1H), 5.68 (dd, 1H), 6.59 (d, 1H), 7.05~7.11 (m, 3H), 7.16 (t, 1H), 7.38 (q, 2H), 7.52 (q, 2H)

Example 19

E-(7-[3-(4-fluorophenyl)-1-isopropyl-1H-indol-2-yl]-[(3R,5S)-3,5-dihydroxy-hept-6-enoic acid])-N-methoxy-N-methyl-amide (compound of Formula 6)

E-(6-{2-[3-(4-fluorophenyl)-1-isopropyl-1H-indol-2-yl]vinyl}-[(4R,6S)-2,2-dimethyl-[1,3]dioxan-4-yl])-N-methoxy-N-methyl-acetamide (5.3 g) and acetonitrile (64.0 mL) were added to a reactor and then the reaction mixture was heated to 40° C. 0.02N Hydrochloric acid solution (11.0 g) was added to the reaction mixture, which was stirred for 15 hours and then concentrated under reduced pressure. Dichloromethane (80.0 mL) and water (60.0 mL) were added to the resulting residue. The separated organic layer was concentrated under reduced pressure to obtain E-(7-[3-(4-fluorophenyl)-1-isopropyl-1H-indol-2-yl]-[(3R,5S)-3,5-dihydroxy-hept-6-enoic acid])-N-methoxy-N-methyl-amide (4.4 g, yield 90%).

¹H-NMR, 400 MHz, CDCl₃, ppm: 1.45~1.50 (m, 1H), 1.58~1.67 (m, 7H), 2.50~2.54 (m, 1H), 2.61 (d, 1H), 3.20 (s, 3H), 3.69 (s, 3H), 4.28 (t, 1H), 4.52 (t, 1H), 4.87 (m, 1H), 5.72 (dd, 1H), 6.70 (d, 1H), 7.05~7.11 (m, 3H), 7.17~7.19 (m, 1H), 7.40 (m, 2H), 7.51 (m, 2H)

Example 20

(3R,5S,6E)-7-[3-(4-fluorophenyl)-1-isopropyl-1H-indol-2-yl]-3,5-dihydroxyhept-6-enoic acid sodium salt (Fluvastatin sodium, compound of Formula 1)

E-(7-[3-(4-fluorophenyl)-1-isopropyl-1H-indol-2-yl]-[(3R,5S)-3,5-dihydroxy-hept-6-enoic acid])-N-methoxy-N-methyl-amide (3.0 g), ethyl alcohol (30.0 mL), and a solution of sodium hydroxide (0.4 g) in water (3.0 mL) were added to a reactor. The reaction mixture was stirred for 16 hours while maintaining the temperature of 20~25° C. and then concentrated under reduced pressure. The resulting residue was dissolved in chloroform (10.0 mL) and then diethyl ether (100.0 mL) was added thereto. The reaction mixture was stirred for over 5 hours and then filtered under reduced pressure. The resulting white solid was dried under vacuum to obtain (3R,5S,6E)-7-[3-(4-fluorophenyl)-1-isopropyl-1H-indol-2-yl]-3,5-dihydroxy hept-6-enoic acid sodium salt (2.4 g, yield 85%).

¹H-NMR, 400 MHz, CD₃OD, ppm: 1.53 (s, 3H), 1.59 (s, 3H), 1.97~2.12 (m, 2H), 2.34~2.55 (m, 2H), 2.35 (s, 1H), 3.09 (s, 1H), 4.23 (m, 1H), 4.34 (m, 1H), 4.68 (m, 1H), 6.34 (dd, 1H), 6.76 (dd, 1H), 7.28~7.59 (m, 8H)

Example 21

E-(6-{2-[2-cyclopropyl-4-(4-fluorophenyl)quinolin-3-yl]vinyl}-[(4R,6S)-2,2-dimethyl-[1,3]dioxan-4-yl])-N-methoxy-N-methyl-acetamide 2-[(4R,6S)-2,2-dimethyl-6-(1-phenyl-1H-tetrazole-5-sulfonylmethyl)-[1,3]dioxan-4-yl]-N-methoxy-N-methyl-acetamide (16.6 g), 2-cyclopropyl-3-formyl-4-(4-fluorophenyl)quinoline (10.0 g), and tetrahydrofuran (400.0 mL) were added to a reactor and then the reaction mixture was cooled to –70° C. A solution of lithium bis(trimethylsilyl)amide in tetrahydrofuran (1M, 36.0 mL) was slowly added to the reaction mixture, the temperature of which was adjusted to –20~–10° C. The reaction mixture was stirred at the same temperature for 1 hour and then 8% sodium bicarbonate solution (80.0 mL) was added thereto under stirring. The separated organic layer was washed with water (60.0 mL) and then concentrated under reduced pressure to obtain E-(6-{2-[2-cyclopropyl-4-(4-fluorophenyl)quinolin-3-yl]vinyl}-[(4R,6S)-2,2-dimethyl-[1,3]dioxan-4-yl])-N-methoxy-N-methyl-acetamide as a solid (15.6 g, yield 90%).

¹H-NMR, 400 MHz, CDCl₃, ppm: 1.05 (d, 2H), 1.35 (m, 2H), 1.43~1.51 (m, 2H), 2.41 (m, 1H), 2.43~2.50 (m, 2H), 3.19 (s, 3H), 3.71 (s, 3H), 4.13 (t, 1H), 4.31 (s, 1H), 4.42 (s, 1H), 5.57 (dd, 1H), 6.62 (d, 1H), 7.14~7.28 (m, 4H), 7.30 (m, 1H), 7.62 (m, 1H), 7.94 (d, 1H)

Example 22

E-6-{2-[2-cyclopropyl-4-(4-fluorophenyl)quinolin-3-yl]vinyl}-(4R,6S)-4-hydroxy-3,4,5,6-tetrahydro-2H-pyran-2-one (compound of Formula 5)

E-(6-{2-[2-cyclopropyl-4-(4-fluorophenyl)quinolin-3-yl]vinyl}-[(4R,6S)-2,2-dimethyl-[1,3]dioxan-4-yl])-N-methoxy-N-methyl-acetamide (3.0 g), acetonitrile (50.0 mL), and sulfuric acid (0.3 mL) were added to a reactor. The reaction mixture was stirred at 50~60° C. for 5 hours and then concentrated under reduced pressure. Ethyl acetate (50.0 mL) and water (50.0 mL) were added to the resulting residue. The separated organic layer was dried under reduced pressure to obtain E-6-{2-[2-cyclopropyl-4-(4-fluorophenyl)quinolin-3-yl]vinyl}-(4R,6S)-4-hydroxy-3,4,5,6-tetrahydro-2H-pyran-2-one (1.2 g, yield 50%).

¹H-NMR, 400 MHz, CDCl₃, ppm: 1.02 (d, 2H), 1.33 (d, 2H), 1.52 (t, 1H), 1.76 (d, 1H), 2.37 (m, 2H), 4.23 (s, 1H), 5.18 (s, 1H), 5.58 (dd, 2H), 6.67 (d, 1H), 7.15~7.18 (m, 4H), 7.27~7.36 (m, 2H), 7.58 (m, 1H), 7.94 (d, 1H)

Example 23

(3R,5S,6E)-7-[2-cyclopropyl-4-(4-fluorophenyl)quinolin-3-yl]-3,5-dihydroxyhept-6-enoic acid 1/2 calcium salt (Pitavastatin calcium, compound of Formula 1)

E-6-{2-[2-cyclopropyl-4-(4-fluorophenyl)quinolin-3-yl]vinyl}-(4R,6S)-4-hydroxy-3,4,5,6-tetrahydro-2H-pyran-2-one (2.0 g), water (20.0 mL), and calcium hydroxide (0.4 g) were added to a reactor. The reaction mixture was stirred at room temperature for 3 hours and then filtered under reduced pressure. The resulting white solid was dried to obtain (3R,5S,6E)-7-[2-cyclopropyl-4-(4-fluorophenyl)quinolin-3-yl]-3,5-dihydroxy hept-6-enoic acid 1/2 calcium salt (2.0 g, yield 91%).

¹H-NMR, 400 MHz, DMSO-d₆, ppm: 0.95~1.55 (m, 2H), 1.35 (t, 3H), 1.70~2.30 (m, 2H), 2.85~3.50 (m, 4H), 3.70~4.35 (m, 1H), 5.25~5.72 (m, 1H), 6.15~6.65 (m, 1H), 6.95~8.10 (m, 8H)

Example 24

E-(7-[2-cyclopropyl-4-(4-fluorophenyl)quinolin-3-yl]-[(3R,5S)-3,5-dihydroxy-hept-6-enoic acid])-N-methoxy-N-methyl-amide (compound of Formula 6)

E-(6-{2-[2-cyclopropyl-4-(4-fluorophenyl)quinolin-3-yl]vinyl}-[(4R,6S)-2,2-dimethyl-[1,3]dioxan-4-yl])-N-methoxy-N-methyl-acetamide (5.9 g) and acetonitrile (100.0 mL) were added to a reactor and then the reaction mixture was heated to 40° C. 0.02N Hydrochloric acid solution (23.0 g) was added to the reaction mixture, which was stirred for 12 hours and then concentrated under reduced pressure. Dichloromethane (80.0 mL) and water (60.0 mL) were added to the resulting residue. The separated organic layer was concentrated under reduced pressure to obtain E-(7-[2-cyclopropyl-4-(4-fluorophenyl)quinolin-3-yl]-[(3R,5S)-3,5-dihydroxy-hept-6-enoic acid])-N-methoxy-N-methyl-amide (5.2 g, yield 95%).

$^1$H-NMR, 400 MHz, CDCl$_3$, ppm: 1.03 (d, 2H), 1.35 (d, 2H), 1.43~1.51 (m, 2H), 2.41 (m, 1H), 2.43~2.57 (m, 2H), 3.19 (s, 3H), 3.68 (s, 3H), 4.15 (t, 1H), 4.42 (s, 1H), 5.57 (dd, 1H), 6.62 (d, 1H), 7.13~7.24 (m, 4H), 7.31 (m, 1H), 7.62 (m, 1H), 7.96 (d, 1H)

Example 25

(3R,5S,6E)-7-[2-cyclopropyl-4-(4-fluorophenyl) quinolin-3-yl]-3,5-dihydroxyhept-6-enoic acid diisopropylamine salt (compound of Formula 8)

E-(7-[2-cyclopropyl-4-(4-fluorophenyl)quinolin-3-yl]-[(3R,5S)-3,5-dihydroxy-hept-6-enoic acid])-N-methoxy-N-methyl-amide (10.3 g), ethyl alcohol (66.0 mL), and a solution of sodium hydroxide (1.4 g) in water (13.0 mL) were added to a reactor. The reaction mixture was stirred for 16 hours while maintaining the temperature of 20~25° C., and then concentrated under reduced pressure. Ethyl acetate (53.0 mL) and water (79.0 mL) were added to the resulting residue under stirring. Ethyl acetate (53.0 mL) was added to the separated water layer, which was then adjusted to pH 3.0~4.0 using 1N hydrochloric acid solution. The separated organic layer was concentrated under reduced pressure. Ethyl acetate (200.0 mL) and diisopropylamine (3.2 mL) were added to the resulting residue. The reaction mixture was stirred at 20~25° C. for over 12 hours and then filtered under reduced pressure. The resulting white solid was dried under vacuum to obtain (3R,5S,6E)-7-[2-cyclopropyl-4-(4-fluorophenyl)quinolin-3-yl]-3,5-dihydroxy hept-6-enoic acid diisopropylamine salt (10.4 g, yield 90%).

$^1$H-NMR, 400 MHz, CDCl$_3$, ppm: 1.02 (d, 2H), 1.26~1.42 (m, 16H), 2.15 (m, 1H), 2.19 (d, 1H), 2.47 (t, 1H), 3.28 (m, 2H), 4.05 (t, 1H), 4.40 (s, 1H), 5.58 (dd, 1H), 6.63 (d, 1H), 7.14~7.22 (m, 4H), 7.29~7.35 (m, 2H), 7.58 (t, 1H), 7.93 (d, 1H)

Example 26

(3R,5S,6E)-7-[2-cyclopropyl-4-(4-fluorophenyl) quinolin-3-yl]-3,5-dihydroxyhept-6-enoic acid 1/2 calcium salt (Pitavastatin calcium, compound of Formula 1)

A solution of (3R,5S,6E)-7-[2-cyclopropyl-4-(4-fluorophenyl)quinolin-3-yl]-3,5-dihydroxy hept-6-enoic acid diisopropylamine salt (10.0 g) in a mixed solvent of ethyl acetate (100.0 mL) and water (100.0 mL) was cooled to 0~5° C. The pH of the reaction mixture was adjusted to 3.0~4.0 using 1N hydrochloric acid solution. Water (40.0 mL) was added to the separated organic layer, the pH of which was then adjusted to 9.0~11.5 using 1N sodium hydroxide solution. Calcium chloride dihydrate (2.8 g) was added to the separated water layer. The reaction mixture was stirred at 20~25° C. for 2 hours and then filtered under reduced pressure. The resulting white solid was dried to obtain (3R,5S,6E)-7-[2-cyclopropyl-4-(4-fluorophenyl)quinolin-3-yl]-3,5-dihydroxy hept-6-enoic acid 1/2 calcium salt (6.9 g, yield 90%).

$^1$H-NMR, 400 MHz, DMSO-d$_6$, ppm: 0.95~1.55 (m, 2H), 1.35 (t, 3H), 1.70~2.30 (m, 2H), 2.85~3.50 (m, 4H), 3.70~4.35 (m, 1H), 5.25~5.72 (m, 1H), 6.15~6.65 (m, 1H), 6.95~8.10 (m, 8H)

The invention claimed is:

1. A process for preparing a compound of Formula 1, comprising converting a compound of Formula 4 to a compound of Formula 1:

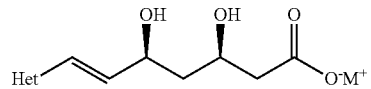

<Formula 1>

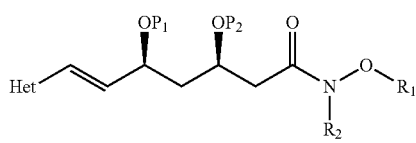

<Formula 4> wherein,

M is an alkali metal or an alkaline earth metal,

R$_1$ and R$_2$ are independently C$_1$~C$_5$ alkyl or aryl,

P$_1$ and P$_2$ are independently an alcohol-protecting group; or P$_1$ and P$_2$ are cyclized each other to form a 1,3-diol protecting group selected from the group consisting of:

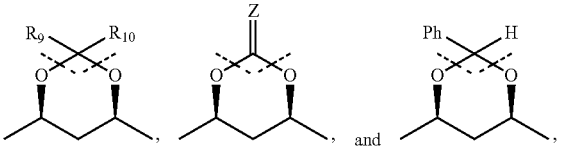

wherein R$_9$ and R$_{10}$ are independently C$_1$~C$_{10}$ alkyl or R$_9$ and R$_{10}$ are cyclized each other to form a pentane ring, a hexane ring, or a heptane ring; Z is oxygen or sulfur; and Ph is phenyl, and Het is

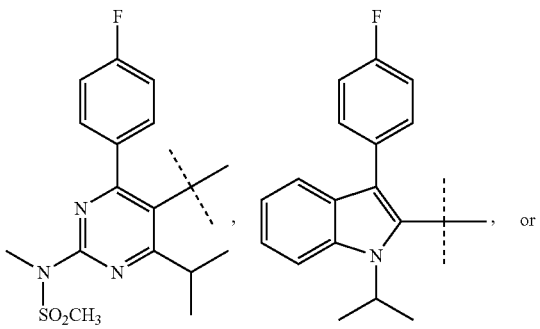

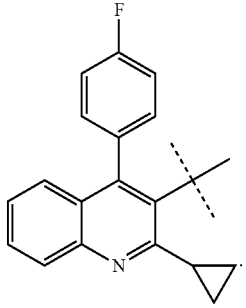

2. The process for preparing a compound of Formula 1 according to claim 1, comprising reacting a compound of Formula 4 with an acid to obtain a compound of Formula 5; and reacting the compound of Formula 5 with an alkali metal hydroxide or an alkaline earth metal hydroxide to obtain a compound of Formula 1:

<Formula 5>

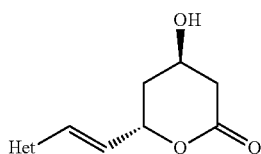

wherein, Het is

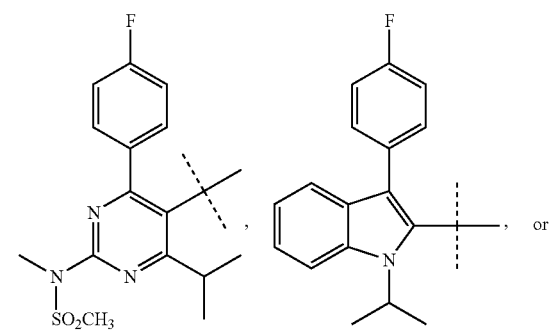

3. The process of claim 2, wherein the acid is selected from the group consisting of hydrochloric acid, sulfuric acid, phosphoric acid, nitric acid, acetic acid, formic acid, sulfonic acid, and a mixture thereof.

4. The process for preparing a compound of Formula 1 according to claim 1, comprising reacting a compound of Formula 4 with an acid to obtain a compound of Formula 6; and hydrolyzing the compound of Formula 6 to obtain a compound of Formula 1:

<Formula 6> wherein, $R_1$, $R_2$ are independently $C_1$~$C_5$ alkyl or aryl, and Het is

5. The process of claim 4, wherein the hydrolyzing is performed by reacting the compound of Formula 6 with an alkali metal hydroxide or an alkaline earth metal hydroxide.

6. The process of claim 4, wherein the acid is selected from the group consisting of hydrochloric acid, sulfuric acid, phosphoric acid, nitric acid, acetic acid, formic acid, sulfonic acid, and a mixture thereof.

7. The process of claim 1, wherein $R_1$ and $R_2$ are independently methyl, ethyl, n-propyl, isopropyl, or phenyl.

8. The process of claim 1, wherein $P_1$ and $P_2$ are cyclized each other to form

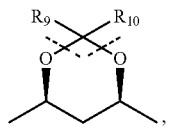

and $R_9$ and $R_{10}$ are independently $C_1$~$C_{10}$ alkyl.

9. The process of claim 1, wherein the compound of Formula 4 has the following structure of Formula 4a:

<Formula 4a>

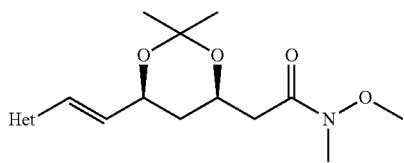

wherein, Het is

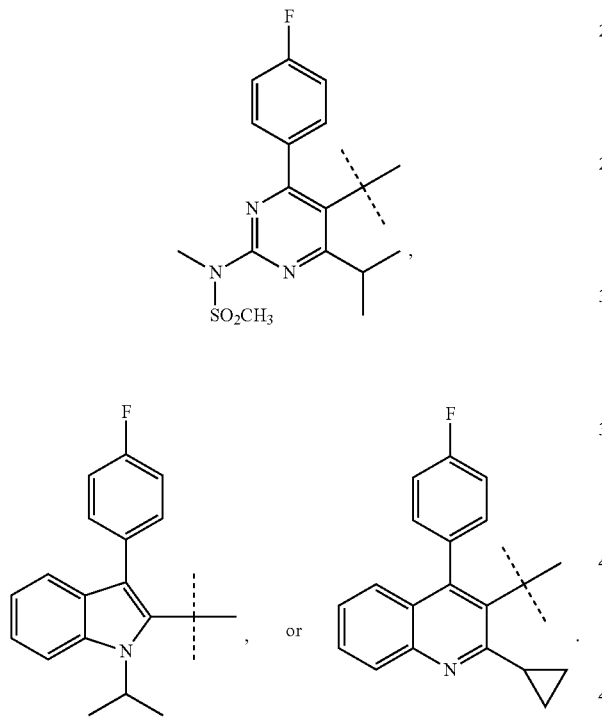

10. The process of claim 1, wherein the compound of Formula 4 is obtained by reacting a compound of Formula 2 and a compound of Formula 3:

<Formula 2>

Het—R

<Formula 3>

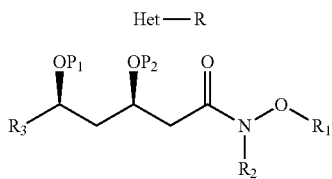

wherein, $R_1$, $R_2$ are independently $C_1$~$C_5$ alkyl or aryl, $P_1$, $P_2$ are independently an alcohol-protecting group; or $P_1$ and $P_2$ are cyclized each other to form a 1,3-diol protecting group selected from the group consisting of:

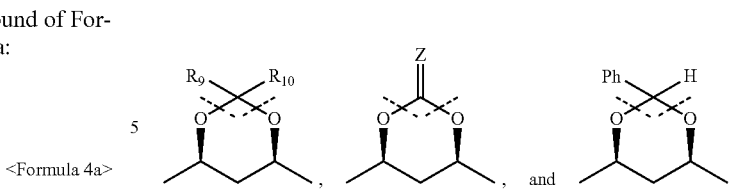

and Het is

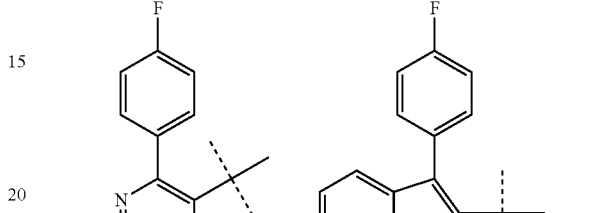

R is —CHO, —CH$_2$P(R$_4$)$_3$Br, —CH$_2$PO(R$_4$)$_2$ or —CH$_2$SO$_2$R$_5$, wherein R$_4$ is C$_1$~C$_6$ alkyl, C$_1$~C$_6$ alkoxy, or aryl, R$_5$ is one of the following groups,

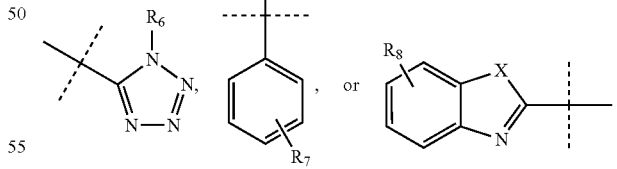

(wherein R$_6$ is C$_1$~C$_6$ alkyl, aryl, aryl-C$_1$~C$_6$ alkyl, or C$_3$~C$_6$ cycloalkyl; R$_7$ is hydrogen, C$_1$~C$_6$ alkyl, aryl, aryl-C$_1$~C$_6$ alkyl, halogen, trifluoromethyl, or nitro; R$_8$ is hydrogen, C$_1$~C$_6$ alkyl, C$_1$~C$_6$ alkoxy, C$_1$~C$_6$ alkyl substituted with halogen, or C$_1$~C$_6$ alkoxy mono- or disubstituted with halogen; X is oxygen, nitrogen, or sulfur), and R$_3$ is —CHO or —CH$_2$SO$_2$R$_5$ (wherein, R$_5$ is the same as defined in the above).

11. A compound of Formula 4:

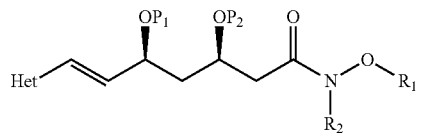

wherein, $R_1$, $R_2$, $P_1$, $P_2$ and Het are the same as defined in claim 1.

12. A compound of Formula 4 of claim 11, having the following structure of Formula 4a:

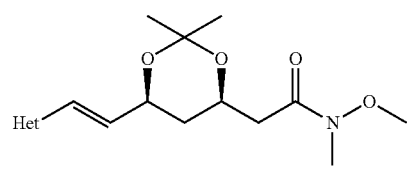

wherein, Het is

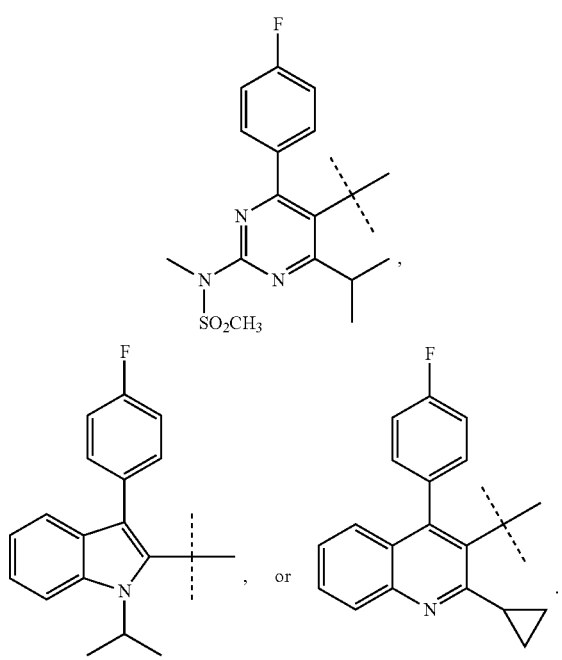

13. A compound of Formula 6:

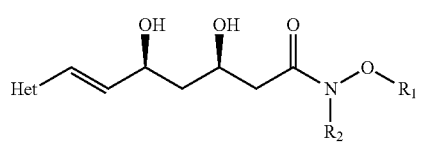

wherein, $R_1$, $R_2$, and Het are the same as defined in claim 1.

14. A compound of Formula 6 of claim 13, having the following structure of Formula 6a:

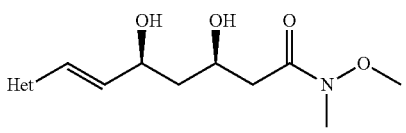

wherein, Het is

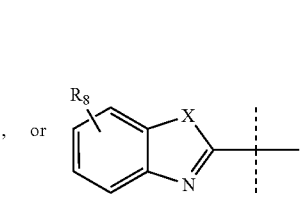

15. A process for preparing a compound of Formula 4, comprising reacting a compound of Formula 2 and a compound of Formula 3:

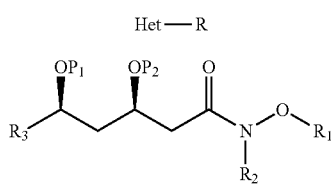

wherein,
$R_1$, $R_2$, $P_1$, $P_2$ and Het are the same as defined in claim 1,
R is —CHO, —CH$_2$P(R$_4$)$_3$Br, —CH$_2$PO(R$_4$)$_2$ or —CH$_2$SO$_2$R$_5$, wherein R$_4$ is C$_1$~C$_6$ alkyl, C$_1$~C$_6$ alkoxy, or aryl, R$_5$ is one of the following compounds,

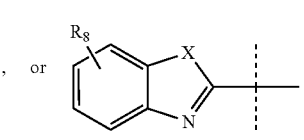

(wherein $R_6$ is $C_1\sim C_6$ alkyl, aryl, aryl-$C_1\sim C_6$ alkyl, or $C_3\sim C_6$ cycloalkyl; $R_7$ is hydrogen, $C_1\sim C_6$ alkyl, aryl, aryl-$C_1\sim C_6$ alkyl, halogen, trifluoromethyl, or nitro; $R_8$ is hydrogen, $C_1\sim C_6$ alkyl, $C_1\sim C_6$ alkoxy, $C_1\sim C_6$ alkyl substituted with halogen, or $C_1\sim C_6$ alkoxy mono- or disubstituted with halogen; X is oxygen, nitrogen, or sulfur), and $R_3$ is —CHO or —$CH_2SO_2R_5$ (wherein, $R_5$ is the same as defined in the above).

16. The process of claim 15, wherein the reacting is performed in the presence of a base selected from the group consisting of sodium $C_1\sim C_6$ alkoxide, potassium $C_1\sim C_6$ alkoxide, sodium carbonate, potassium carbonate, lithium carbonate, cesium carbonate, sodium bicarbonate, potassium bicarbonate, potassium phosphate, 1,8-diazabicyclo[5.4.0]undec-7-ene (DBU), 1,4-diazabicyclo[2.2.2]octane (DABCO), 1,5-diazabicyclo[4.3.0]non-5-ene (DBN), pyridine, dimethylaminopyridine, triethylamine, lithium bis(trimethylsilyl)amide, sodium bis(trimethylsilyl)amide, potassium bis(trimethylsilyl)amide, butyllithium, sodium hydride, and a mixture thereof.

17. The process of claim 15, wherein the reacting is performed in the presence of a solvent selected from the group consisting of dimethylformamide, dimethylacetamide, dichloromethane, dimethyl sulfoxide, tetrahydrofuran, hexamethylphosphoramide, $C_1\sim C_4$ alcohol, dimethyl ether, diethyl ether, diisopropyl ether, ethyl acetate, dimethoxyethane, toluene, and a mixture thereof.

18. A compound of Formula 3:

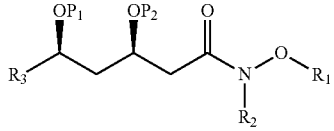

<Formula 3> wherein, $R_1$, $R_2$, $P_1$ and $P_2$ are the same as defined in claim 1, and $R_3$ is —$CH_2SO_2R_5$ (wherein, $R_5$ is one of the following compounds,

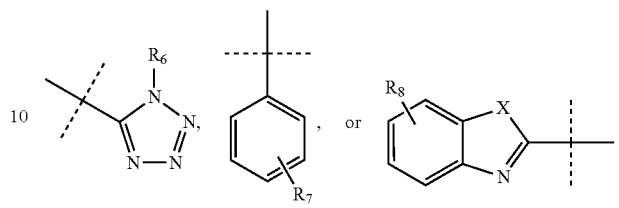

wherein $R_6$ is $C_1\sim C_6$ alkyl, aryl, aryl-$C_1\sim C_6$ alkyl, or $C_3\sim C_6$ cycloalkyl; $R_7$ is hydrogen, $C_1\sim C_6$ alkyl, aryl, aryl-$C_1\sim C_6$ alkyl, halogen, trifluoromethyl, or nitro; $R_8$ is hydrogen, $C_1\sim C_6$ alkyl, $C_1\sim C_6$ alkoxy, $C_1\sim C_6$ alkyl substituted with halogen, or $C_1\sim C_6$ alkoxy mono- or disubstituted with halogen; X is oxygen, nitrogen, or sulfur).

19. A compound of Formula 3 of claim 18, having the following Formula 3a:

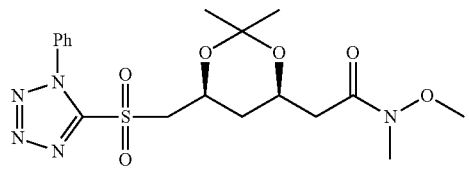

<Formula 3a> wherein, Ph is phenyl.

* * * * *